(12) United States Patent
Vogel et al.

(10) Patent No.: US 9,308,169 B2
(45) Date of Patent: *Apr. 12, 2016

(54) MICROSPHERES FOR ACTIVE EMBOLIZATION

(75) Inventors: Jean-Marie Vogel, Boxborough, MA (US); Egisto Boschetti, Gougenot (FR)

(73) Assignee: Biosphere Medical, Inc., South Jordan, UT (US)

( * ) Notice: Subject to any disclaimer, the term of this patent is extended or adjusted under 35 U.S.C. 154(b) by 102 days.

This patent is subject to a terminal disclaimer.

(21) Appl. No.: 13/462,004

(22) Filed: May 2, 2012

(65) Prior Publication Data

US 2012/0213831 A1    Aug. 23, 2012

Related U.S. Application Data

(63) Continuation of application No. 10/220,982, filed as application No. PCT/US01/09619 on Mar. 23, 2001, now Pat. No. 8,697,137.

(60) Provisional application No. 60/191,899, filed on Mar. 24, 2000.

(51) Int. Cl.
| | |
|---|---|
| *A61K 9/50* | (2006.01) |
| *A61K 9/16* | (2006.01) |
| *A61K 31/715* | (2006.01) |
| *A61K 45/06* | (2006.01) |

(52) U.S. Cl.
CPC .............. *A61K 9/1635* (2013.01); *A61K 31/715* (2013.01); *A61K 45/06* (2013.01); *A61L 2430/36* (2013.01); *Y10T 428/2982* (2015.01)

(58) Field of Classification Search
CPC ....................................................... A61K 9/50
USPC ........................ 424/422, 489, 401, 490, 501
See application file for complete search history.

(56) References Cited

U.S. PATENT DOCUMENTS

| | | | | |
|---|---|---|---|---|
| 5,202,352 | A | * | 4/1993 | Okada et al. .................. 514/475 |
| 5,514,379 | A | * | 5/1996 | Weissleder et al. ........... 424/426 |
| 6,315,709 | B1 | | 11/2001 | Garibaldi et al. |
| 7,407,646 | B2 | | 8/2008 | Laurent et al. |
| 2003/0077225 | A1 | | 4/2003 | Laurent et al. |
| 2005/0058603 | A1 | | 3/2005 | Gao et al. |
| 2011/0076231 | A1 | | 3/2011 | Schwarz et al. |
| 2011/0280947 | A1 | | 11/2011 | Rioux et al. |

FOREIGN PATENT DOCUMENTS

JP          6056676      *    3/1994

OTHER PUBLICATIONS

Kitamura et al, Sumika gel, Sumitomo Chemical special Issue, 1980, pp. 1-9.*

Jiaqi. Nippon Acta Radiologica, 58 (1), pp. 19-24, 1996.*
Hori et al Intervent. Radiology, vol. 11, # 3, 1996, pp. 1-12.*
International Search Report and Written Opinion dated Aug. 23, 2013 for PCT/US2013/042363.
Laurent, 'Microspheres and Nonspherical Particles for Embolization,' Techniques in Vascular and Interventional Radiology, vol. 10, pp. 248-256, 2007.
Raoul et al., 'Hepatic Artery Injection of I-131-Labeled Lipiodol: Part I: Biodistribution Study Results in Patients with Hepatocellular Carcinoma and Liver Metastases', Radiololgy 168(2): 541-545, Aug. 1988.
Raoul et al., 'Chemoembolization of Hepatocellular Carcinomas. A Study fo the Biodistribution and Pharmacokinetics of Doxorubicin', Cancer 70(3): 585-590, Aug. 1992.
de Baere et al., 'Quantification of Tumor Uptake of Iodized Oils and Emulsions of Iodized Oils: Experimental Study', Radiology 201: 713-735, 1996.
Hong et al., 'Effects fo the Type of Embolization Particles on Carboplatin Concentration in Liver Tumors After Transcatheter Arterial Chemoembolization in a Rabbit Model of Liver Cancer', J Vasc Interv Radiol 16(12): 1711-1717, 2005.
Namur et al., 'MR Imaging Detection of Superparamagnetic Iron Oxide-Loaded Tris-Acryl Embolization Microspheres', J Vasc Interv Radiol, 18(10): 1287-95, Oct. 2007.
D'Souza et al., 'Methods to Assiss In Vitro Drug Release from Injectable Polymeric Particulate Systems', Pharmaceutical Research, 23(3): 460-74, Mar. 2006.
Kotanski et al., 'A Novel In Vitro Release Technique for Peptide-Containing Biodegradable Microspheres', AAPS PharSciTech, Article 4, 2000.
Haacke et al., 'Susceptibility Weighted Imaging (SWI)', Magnetic Resonance in Medicine 52(3): 612-618, 2004.
Haacke et al., 'Characterizing Iron Deposition in Multiple Sclerosis Lesions Using Susceptibility Weighted Imaging', 29(3): 537-544, 2009.
Namur et al., 'Tissular Distribution and Concentration of Doxorubicin in Pig Liver After Embolization with Drug Eluting Beads', Society fo Interventional Radiology, SIR Washington, Mar. 2008.
Namur et al, 'Diffusion of doxorubicin from Drugs Eluting Beads and Tissular Changes After Embolization in Hepatocellular Carcinoma', Society of Interventional Radiology—SIR San Diego, CA, JVIR book of Abstracts, p. S61, Mar. 2009.
Lee et al., 'Distribution of Iron Oxide-Containing Embosphere Particles After Transcatheter Arterial Embolization in an Animal Model of Liver Cancer: Evaluation with MR Imaging and Implication for Therapy', J Vasc Interv Radiol, 19(10): 1490-1496, Oct. 2008.

\* cited by examiner

*Primary Examiner* — Gollamudi Kishore
(74) *Attorney, Agent, or Firm* — Stoel Rives LLP

(57) ABSTRACT

The present invention relates to injectable compositions comprising biocompatible, swellable, substantially hydrophilic, non-toxic and substantially spherical polymeric material carriers which are capable of efficiently delivering bioactive therapeutic factor(s) for use in embolization drug therapy. The present invention further relates to methods of embolization gene therapy, particularly for the treatment of angiogenic and non-angiogenic-dependent diseases, using the injectable compositions.

25 Claims, No Drawings

MICROSPHERES FOR ACTIVE EMBOLIZATION

RELATED APPLICATIONS

This application is a continuation of co-pending U.S. patent application Ser. No. 10/220,982, filed Dec. 12, 2002, titled "MICROSPHERES FOR ACTIVE EMBOLIZATION," which is a National Stage Entry of International Application No. PCT/US01/09619, filed on Mar. 23, 2001, which claims the benefit of U.S. Provisional Application Ser. No. 60/191,899, filed Mar. 24, 2000, each of which is incorporated herein by reference in its entirety.

1. FIELD OF INVENTION

The present invention relates to compositions and methods for treating diseases including cancer and various other angiogenic-dependent diseases, and more particularly to compositions comprising bioactive therapeutic factors in association with microspheres as carriers (which have been coated with or otherwise contain such factors), as well as methods for using such compositions for active embolization therapy.

BACKGROUND OF INVENTION 2.1 Angiogenesis-Dependent Diseases

Angiogenesis-dependent diseases (i.e., those diseases which require or induce vascular growth) represent a significant portion of all diseases for which medical treatment is sought. For example, cancer remains the second leading cause of death in the United States, and accounts for over one-fifth of the total mortality. Briefly, cancer is characterized by the uncontrolled division of a population of cells which, most typically, leads to the formation of one or more tumors. Such tumors are also characterized by the ingrowth of vasculature which provide by blood circulation various factors that permit continued tumor growth. Although cancer is generally more readily diagnosed than in the past, many forms, even if detected early, are still incurable.

A variety of methods are presently utilized to treat cancer, including for example, various surgical procedures. If treated with surgery alone however, many patients (particularly those with certain types of cancer, such as breast, brain, colon and hepatic cancer) will experience recurrence of the cancer. Therefore, in addition to surgery, many cancers are also treated with a combination of therapies involving cytotoxic chemotherapeutic drugs (e.g., vincristine, doxorubicin, taxol, vinblastine, cisplatin, methotrexate, 5-FU, etc.) and/or radiation therapy. One difficulty with this approach, however, is that radiotherapeutic and chemotherapeutic agents are toxic to normal tissues, and often create life-threatening side effects. In addition, these approaches often have extremely high failure/remission rates.

In addition to surgical, chemo- and radiation therapies, others have attempted to utilize an individual's own immune system in order to eliminate cancerous cells. For example, some have suggested the use of bacterial or viral components as adjuvants in order to stimulate the immune system to destroy tumor cells. (See generally "Principles of Cancer Biotherapy," Oldham (ed.), Raven Press, New York, 1987.) Such agents have generally been useful as adjuvants and as nonspecific stimulants in animal tumor models, but have not as of yet proved to be generally effective in humans.

One additional limitation of present methods is that local recurrence and local disease control remains a major challenge in the treatment of malignancy. In particular, a total of 630,000 patients annually (in the U.S.) have localized disease (no evidence of distant metastatic spread) at the time of presentation; this represents 64% of all those patients diagnosed with malignancy (this does not include nonmelanoma skin cancer or carcinoma in situ). For the vast majority of these patients, surgical resection of the disease represents the greatest chance for a cure and indeed 428,000 will be cured after the initial treatment—428,000. Unfortunately, 202,000 (or 32% of all patients with localized disease) will relapse after the initial treatment. Of those who relapse, the number who will relapse due to local recurrence of the disease amounts to 133,000 patients annually (or 21% of all those with localized disease). The number who will relapse due to distant metastases of the disease is 68,000 patients annually (11% of all those with localized disease). Approximately another 102,100 patients annually will die as a direct result of an inability to control the local growth of the disease. Examples of cancers which illustrate the problem patients are faced with are breast cancer and liver cancer.

Breast Cancer

This problem is particularly evident for breast cancer which is a disease which affects approximately 186,000 women annually in the U.S. and for which the mortality rate has remained unchanged for 50 years. Surgical resection of the disease through radical mastectomy, modified radical mastectomy, or lumpectomy still remains the mainstay of treatment for this disease. Unfortunately, 39% of those treated with lumpectomy alone will develop a recurrence of the disease, and surprisingly, so will 25% of those in which the resection margin is found to be clear of tumor histologically. As many as 90% of these local recurrences will occur within 2 cm of the previous excision site.

Liver Cancer

Over 1.2 million people died in 1999 from primary liver cancer, the majority of them in Asia. Primary liver cancer refers to liver cancer in which the initial cancerous cells are formed in the liver, rather than traveling to the liver from some other cancer site in the body. Patients with certain forms of hepatitis, including hepatitis C, a viral disease which causes inflammation of the liver, are known to be at great risk for primary liver cancer. The incidence of primary liver cancer is expected to increase dramatically in the United States, where estimates have indicated that more than 4 million people are now hepatitis C positive.

Over 70 percent of primary liver cancers are inoperable and are treated with radiation or chemotherapy. The currently available treatment options include the following:

Chemotherapy:

Chemotherapy seeks to control cancer by killing rapidly dividing cancer cells. However, a number of non-cancerous cells in the body, such as bone marrow cells, also rapidly divide and are, therefore, highly susceptible to being inadvertently killed by the chemotherapy. Thus, doses sufficient to eradicate the cancer often cause life-threatening side effects due to the destruction of non-cancerous cells.

Chemoembolization and Various Treatments Under Development:

For example, precutaenous ethanol injection is a painful procedure which only works for small tumors which are limited to smaller than 3-4 cm.

Transplantation:

Transplantation is also an available therapy which is expensive and limited by the availability of organs and which can still lead to a recurrence of the tumor. Also, there are recurring dangers associated with invasive surgery.

Moreover, chemotherapy may also damage the natural anti-tumor defense of the human body.

Uterine Fibroids

A relevant example of a non-cancerous tumor would be uterine fibroids, also known as leiomyomas. These are non-cancerous tumors composed of certain types of muscle fibers and fibrous connective tissue. The cause of uterine fibroids is unknown. Most patients with uterine fibroids do not initially have symptoms and remain untreated until the patient experiences abnormal bleeding, urinary frequency, pain, swelling and difficulty with fertility. Approximately 25 million women in the United States have uterine fibroids, and approximately 5.5 million of these women are symptomatic enough to seek treatment each year. Until now, women suffering from uterine fibroids have had few viable treatment options, including hysterectomy, myomectomy, and Medical Management and "Watch and Wait". The therapies currently available for treating uterine fibroids have significant drawbacks including: temporary or permanent loss of fertility for women of childbearing age, lengthy recovery periods, adverse psychological effects which may lead to early menopause, high costs, including costs of medications, surgical procedures, frequent and long hospital stays, discomfort and side effects from invasive surgical procedures and hormone therapy, and/or risk of recurrence of the fibroids.

As a result, there is a significant need for a uniformly efficacious therapy program for patients with, inter alia, breast cancer, liver cancer, pancreatic cancer and uterine fibroids.

Passive Embolization

One method that has been attempted for the treatment of tumors albeit with limited success is passive embolization. Briefly, blood vessels which nourish a tumor are deliberately blocked by injection of an embolic material into the vessels. A variety of materials have been attempted in this regard, including autologous substances such as fat, blood clot, and chopped muscle fragments, as well as artificial materials such as wool, cotton, steel balls, plastic or glass beads, tantalum powder, silicone compounds, radioactive particles, sterile absorbable gelatin sponge (Sterispon, Gelfoam), oxidized cellulose (Oxycel), steel coils, alcohol, lyophilized human dura mater (Lyodura), microfibrillar collagen (Avitene), collagen fibrils (Tachotop), polyvinyl alcohol sponge (PVA; Ivalon), Barium-impregnated silicon spheres (Biss) and detachable balloons. The size of tumor metastases may be temporarily decreased utilizing such methods, but tumors typically respond by causing the growth of new blood vessels into the tumor.

A related problem to cancer tumor formation is the development of cancerous blockages which inhibit the flow of material through body passageways, such as the bile ducts, trachea, esophagus, vasculature and urethra. One device, the stent, has been developed in order to hold open passageways which have been blocked by tumors or other substances. Representative examples of common stents include the Wallstent, Strecker stent, Gianturco stent, and the Palmaz stent. The major problem with stents, however, is that they do not prevent the ingrowth of tumor or inflammatory material through the interstices of the stent. If this material reaches the inside of a stent and compromises the stent lumen, it may result in blockage of the body passageway into which it has been inserted. In addition, presence of a stent in the body may induce reactive or inflammatory tissue (e.g., blood vessels, fibroblasts, white blood cells) to enter the stent tureen, resulting in partial or complete closure of the stent.

2.2 Therapeutic or Active Embolization

The administration of cytotoxic drug into the proximity of a tumor increases the ratio of tumor to normal tissue delivery. Such regional administration can be accomplished by directly delivering drugs into the tumor via its blood supply or into the body cavity where the particular tumor is located. Regional drug perfusion has the advantage of increasing peak drug concentrations to the target tissue but exposure is limited to the first pass of blood through the organ being perfused. The portion of the drug not taken up by the initial pass circulates systemically and is then taken up by the normal tissues.

Therapeutic vascular occlusions (embolizations) are techniques used to treat certain pathological conditions in situ. They are practiced generally by means of catheters making it possible, under imagery control, to position particulate occlusion agents (emboli) in the circulatory system. They can also concern the vessels of various processes: tumors, vascular malformations, hemorrhagic processes, etc. Notably in the case of tumors, vascular occlusion can suppress pain, limit blood loss on the surgical intervention to follow embolization or even bring on a tumoral necrosis and avoid the operation. In the case of vascular malformations, it enables the blood flow to the normal tissues to be normalized, aids in surgery and limits the risk of hemorrhage. In hemorrhagic processes, vascular occlusion produces a reduction of flow, which promotes cicatrization of the arterial opening(s).

Furthermore, depending on the pathological conditions treated, embolization can be carried out for temporary as well as permanent objectives.

Different types of emboli are known in the prior art. In particular, liquid agents (acrylic glues, gels, viscous suspensions, etc.) or particulate agents (miscellaneous polymers, dura mater, gelatin sponges, spheres, balloons, spirals, etc.) can be involved. The major disadvantages of the known liquid emboli reside in their toxicity to the tissues, which can generate necrosis phenomena, and in the risk of sticking of the catheters. Another limitation of liquid emboli is that they act only in a passive way and are not capable of being used for drug delivery.

The dual functions of the regional distribution of drugs to and the minimization of loss from the target site can be achieved with microspheres. When introduced via a regional artery, such microspheres are trapped within the vasculature of tissues, where they release their drug load. Such dual action is referred to as active embolization. Microspheres may be of either a solid or porous composition, and can be made to contain dispersed drug molecules either in solution or solid form (Zimmer and Kreuter, 1995). Microspheres have special application in treating tumors located within organs supplied by a single afferent arterial blood supply, for example, the liver (Chen et al. 1994). They are of most value in cases where the tumor in the target organ is the only region that requires therapy.

While studies relating to the use of microspheres for embolization drug-based therapy are known, relatively few studies have been performed with microspheres for use in gene therapy. For instance, glass beads are commonly used in the selective extraction of DNA from heterogenous mixtures via electrostatic attraction. While hydroxyapetite has also been utilized for purification of nucleic acids (Kumazawa et al. 1992) and hydroxyapetite spheres have been used for sustained release of doxorubicin by direct implantation into hepatic tumors via ultrasonic guidance (Kunieda et al., 1993), other studies reveal that this particular matrix may indeed be unsuitable for exposure to mammalian tissue (Dass et al., 1997a, 1997b). DNA has also been retained on PDB microspheres with diethylaminoethyl (DEAE) functional groups at the surface (Katz et al, 1990; Maa et al., 1990).

Thus, there is a demonstrated need for the further development of microspheres for gene delivery. The major desired advantage is the ability to specifically target the anticancer agent to the tumor vasculature by the blood flow. Further, the obstruction of tumor blood supply, with the simultaneous disruption in nutrient supply and waste removal, is perhaps the most desired result for destruction of the tumor cells.

SUMMARY OF INVENTION

In one embodiment, the invention provides compositions and methods for delivery of drugs, vaccines, polynucleotides, and diagnostic or imaging agents to a mammal, using a wide variety of polymeric materials as carriers for the aforesaid agents. In a preferred embodiment, the invention provides microparticles for the delivery of these agents, particularly, microspheres. In a most preferred embodiment, the invention provides microparticles for the delivery of polynucleotides using a transfection agent.

More specifically, in the preferred embodiment, the polymeric material carrier for use in the present invention encompasses any particle that must be able to "carry" or be associated with a bioactive therapeutic factor and a transfection agent of the present invention. The preferred polymeric material is based on substantially spherical, substantially hydrophilic, inert, ionic and cross-linked polymers of a size sufficient to embolize and release the bioactive therapeutic factor. In a preferred embodiment, the bioactive therapeutic factor is physically linked to the transfection agent, which is also linked to the microparticle.

In one embodiment, the present invention provides bioactive therapeutic compositions, as well as methods and devices which utilize such compositions for the treatment of cancer and various other angiogenesis-dependent diseases including precancerous disorders. Within one aspect of the present invention, compositions are provided comprising (a) a bioactive therapeutic factor, (b) a polymeric material carrier, and (c) a transfection agent.

Within another preferred aspect of the present invention, compositions are provided comprising (a) a polynucleotide encoding a bioactive therapeutic factor, (b) a polymeric material carrier, and (c) a transfection agent.

Within another preferred aspect of the invention, compositions are provided comprising (a) a polynucleotide encoding a bioactive therapeutic factor, (b) a polymeric material carrier, and (c) a lipopolyamine transfection agent.

A wide variety of molecules may be utilized within the scope of the present invention as bioactive therapeutic factors, including for example, without limitation, anti-angiogenic factors, antineoplastic agents, peptides and peptide analogs, antibodies or fragments thereof, vaccines, enzymes, nucleic acids, RNA and DNA, of either natural or synthetic origin, including recombinant RNA and DNA and antisense RNA and DNA; hammerhead RNA, ribozymes, antigene nucleic acids, both single and double stranded RNA and DNA and analogs thereof.

The polymeric materials of the present invention include, but are not limited to, acrylic polymers, vinyl alcohol polymers, acrylate polymers, poly (lactic acid), polyacrylamides, poly(anhydrides), polysaccharides, silicones, or mixtures thereof. More preferably, the polymeric materials are substantially hydrophilic crosslinked copolymers of the acrylic family such as polyacrylamides and their derivatives, polyacrylates and their derivatives as well as polyallyl and polyvinyl compounds. All of these polymers are crosslinked so as to be stable and non-resorbable.

Within the various embodiments disclosed herein of the present invention, the bioactive therapeutic factor is physically associated with the transfection agent and the bioactive therapeutic factor-transfection agent complex is physically associated with the polymeric carrier. The bioactive therapeutic factor is preferably adsorbed by means of association forces that are well known in liquid adsorption chromatography including such association forces as, without limitation, ion exchange, hydrophobicity, molecular recognition or combinations thereof. In one preferred embodiment the bioactive therapeutic factor is associated with the transfection agent to form a complex prior to mixing or contacting with the polymeric carrier of the present invention.

In one aspect of the present invention, the selected bioactive therapeutic factor is mixed with the transfecting agent so as to form a complex between the bioactive therapeutic factor and the transfecting agent which imparts specific properties to the complex, such as increased hydrophobicity.

In another aspect of the invention, the polymeric material carrier is mixed together with a sufficient amount of a transfectable bioactive therapeutic factor. The physical association between the bioactive therapeutic factor and the polymeric material carrier is the result of ionic and hydrophobic associations that can be enhanced by the addition of salts such as, for example, without limitation, sodium chloride or contrast media such as salts containing barium or iodide.

Within the various embodiments disclosed herein of the present invention, once delivered to the appropriate site, the bioactive therapeutic factor-transfection agent complexes adsorbed on the surface of the embolic material are progressively desorbed and delivered into the surrounding cells by a variety of mechanisms including, for example, without limitation, spontaneous endocytosis, receptor-mediated endocytosis, endosomolysis, and cell membrane destabilization or combinations thereof. The desorption of the bioactive therapeutic factor is induced by natural components of biological liquids that serve to weaken the adsorption strength between the embolic material and the bioactive therapeutic factor until the total desorption of the latter is achieved. The desorption of the bioactive therapeutic factor can also be modulated by the use of linkages which are hydrolyzable in vivo, including, without limitation, ester or osidic linkages. In other various embodiments the desorption of the bioactive therapeutic factor can also be modulated by the use of peptides in association with the bioactive therapeutic factor wherein the peptide linkage is capable of cleavage with cellular proteolytic enzymes.

Within another aspect of the present invention, methods are provided for embolizing a blood vessel, comprising administering to the vessel of a patient in need thereof a therapeutically effective amount of a bioactive therapeutic factor, such that the blood vessel is effectively occluded. Within one embodiment, the bioactive therapeutic factor is simultaneously or sequentially delivered to a blood vessel which nourishes a tumor.

Within another aspect of the present invention, methods are provided for embolizing blood vessels in tumorigenic, angiogenesis-dependent diseases, comprising administering to a patient in need thereof a therapeutically effective amount of a composition comprising a polynucleotide encoding a bioactive therapeutic factor, wherein the polynucleotide is associated with a transfection agent, and wherein said polynucleotide-transfection agent is further associated with a polymeric material carrier, such that the blood vessel is effectively occluded.

Within another more preferred aspect of the present invention, methods are provided for embolizing blood vessels in tumorigenic, angiogenesis-dependent diseases, comprising administering to a patient in need thereof a therapeutically effective amount of a composition comprising a polynucleotide encoding a bioactive therapeutic factor, wherein the polynucleotide is associated with a lipopolyamine transfection agent, wherein said associated polynucleotide-transfection agent is further associated with a substantially hydrophilic microsphere, such that the blood vessel is effectively occluded.

Within another aspect of the present invention, methods are provided for embolizing blood vessels in tumorigenic, angiogenesis-dependent diseases, comprising administering to a patient in need thereof a therapeutically effective amount of a composition comprising a viral vector or virus-like particle containing a polynucleotide encoding a bioactive therapeutic factor, wherein the viral vector or virus-like particle is associated with a transfection agent, and wherein said associated viral vector-transfection agent is further associated with a substantially hydrophilic microsphere, such that the blood vessel is effectively occluded.

Within another more preferred aspect of the present invention, methods are provided for embolizing blood vessels in tumorigenic, angiogenesis-dependent diseases, comprising administering to a patient in need thereof a therapeutically effective amount of a composition comprising a viral vector or virus-like particle containing a polynucleotide encoding a bioactive therapeutic factor wherein the viral vector or virus-like particle is associated with a lipolyamine transfection agent, and wherein said associated viral vector-transfection agent is further associated with a substantially hydrophilic microsphere, such that the blood vessel is effectively occluded.

Within yet another aspect of the present invention, methods are provided for inhibiting angiogenesis in patients with non-tumorigenic, angiogenesis-dependent diseases, comprising administering to a patient with a non-tumorigenic angiogenesis-dependent disease in need thereof a therapeutically effective amount of a drug together with a polynucleotide encoding a bioactive therapeutic factor, wherein said polynucleotide is associated with a transfection agent, and wherein said associated polynucleotide-transfection agent is further associated with a polymeric material carrier such that the formation of new blood vessels is inhibited. In another aspect of the present invention, such a drug may be incorporated within the polymeric material carrier so as not to interfere with the transfer of the bioactive therapeutic factor being simultaneously administered.

Within yet another aspect of the present invention, methods are provided for treating patients with non-tumorigenic, non-angiogenesis-dependent diseases, comprising administering to a patient in need thereof a therapeutically effective amount of a drug together with a polynucleotide encoding a bioactive therapeutic factor associated with a transfection agent, wherein said drug is contained within the polymeric material carrier so as not to interfere with the transfer of the bioactive therapeutic factor associated with the polymeric material carrier being simultaneously administered, such that the symptoms of the non-tumorigenic, non-angiogenesis-dependent disease are ameliorated.

Within other preferred embodiments, the compositions of the present invention comprise (a) a polynucleotide encoding a bioactive therapeutic factor, (b) a polymeric material carrier, and (c) a lipopolyamine transfection agent together with a lighter d group transition metal (e.g., a vanadium species, molybdenum species, tungsten species, titanium species, niobium species or tantalum species) which inhibits the formation of new blood vessels.

Within other preferred embodiments, the compositions of the present invention comprise (a) a polynucleotide encoding a bioactive therapeutic factor, (b) a cationic cross-linked microparticle, and (c) a lipopolyamine transfection agent together with a transfection enhancing agent.

Within another preferred embodiment, a method is provided for delivering to a mammalian host a polynucleotide which comprises administering to a mammal having a disease a substantially hydrophilic polymeric material associated with a polynucleotide and a transfection agent. Embodiments of the latter method are provided wherein the administration of said substantially hydrophilic polymeric material associated with a polynucleotide and a transfection agent is for gene therapy, wherein the polymeric material microsphere is of a size sufficient to embolize the vessels at the site of administration, and wherein the polymeric material is not of sufficient size to embolize the vessels at the site of administration but is sufficient to anchor in the tumor.

Within another preferred embodiment, a method is provided for active embolization in a mammal host which comprises administering to a mammal having an angiogenesis dependent disease a substantially hydrophilic polymeric material associated with a bioactive therapeutic factor capable of expression of an anti-angiogenic material, wherein said bioactive therapeutic factor is associated with a transfection agent.

Within another aspect of the present invention, methods are provided for treating tumor excision sites, comprising administering a polymeric material carrier bioactive therapeutic factor associated with a transfection agent composition as described above to the resection margins of a tumor subsequent to excision, such that the local recurrence of cancer and the formation of new blood vessels at the site is inhibited.

Within other aspects, methods are provided for embolizing blood vessels in non-tumorigenic, angiogenesis-dependent diseases, comprising delivering to the vessel a therapeutically effective amount of a composition comprising a drug in conjunction with a polynucleotide encoding a bioactive therapeutic factor, such that the blood vessel is effectively occluded.

Within another aspect of the present invention, methods are provided for embolizing blood vessels in tumorigenic, angiogenesis-dependent diseases, comprising delivering to the vessel a therapeutically effective amount of a composition comprising a drug in conjunction with a polynucleotide encoding a bioactive therapeutic factor, such that the blood vessel is effectively occluded and the polynucleotide encoding a bioactive therapeutic factor is delivered into the cell for expression.

Within another aspect of the present invention, a method is provided for active embolization in a mammal host which comprises administering to a mammal having a disease a substantially hydrophilic polymeric material associated with a bioactive therapeutic factor, wherein said bioactive therapeutic factor is associated with a transfection agent.

Within another aspect of the present invention, a microparticle is provided which is suitable for active embolization which comprises a polymeric material capable of embolizing a blood vessel, wherein said polymeric material is linked to a transfection agent which is linked to a genetic material.

Within other aspects, methods are provided for treating neovascular diseases of an organ including, for example, without limitation, the eye, comprising administering to a patient in need thereof a therapeutically effective amount of a bioactive therapeutic factor to the eye, for example, such that the formation of new blood vessels is inhibited.

The present invention provides compositions and methods suitable for treating cancers, as well as other non-tumorigenic angiogenesis-dependent diseases, and further provides other related advantages. Such cancers include, without limitation, liver, ovarian, kidney, pancreatic, prostate, skin cancer, head and neck tumors, breast tumors, and Kaposi's sarcoma, and superficial forms of bladder cancer. In addition to cancer, however, numerous other non-tumorigenic angiogenesis-dependent diseases which are characterized by the abnormal growth of blood vessels may also be treated with the bioactive therapeutic factors or compositions of the present invention. Representative examples of such non-tumorigenic angiogenesis-dependent diseases include, without limitation, hypertrophic scars and keloids, proliferative diabetic retinopathy, rheumatoid arthritis, arteriovenous malformations, atherosclerotic plaques, delayed wound healing, hemophilic joints, nonunion fractures, Osier-Weber syndrome, psoriasis, pyogenic granuloma, scleroderma, tracoma, menorrhagia and vascular adhesions.

Within another embodiment of the invention are provided kits for performing embolization gene therapy comprising: (a) a suspension of microspheres suitable for embolization; and (b) a transfection agent suitable for delivering genetic material to a cell. Within another further embodiment of the invention, kits are provided wherein the polymeric material is contained within one vial and the transfection agent associated with a polynucleotide which encodes the bioactive therapeutic factor is contained within another vial, and wherein the contents of both vials are mixed together to form the pharmaceutical composition. Within another further embodiment of the invention, kits are provided wherein the polymeric material is contained within one vial, the transfection agent is contained within another separate vial, and the polynucleotide which encodes the bioactive therapeutic factor is contained within another separate vial, wherein the contents of all three vials are mixed together to form the pharmaceutical composition. Within another further embodiment of the invention, kits are provided wherein the components of (a) a suspension of microspheres suitable for embolization; and (b) a transfection agent suitable for delivering genetic material to a cell, are in one vial.

These and other aspects of the present invention will become evident upon reference to the following detailed description and attached drawings. In addition, various references are set forth below which are incorporated herein by reference in their entirety.

4. DETAILED DESCRIPTION OF THE INVENTION

Definitions

As used herein, "substantially spherical" generally means a shape that is close to a perfect sphere, which is defined as a volume that presents the lowest external surface area. Specifically, "substantially spherical" in the present invention means, when viewing any cross-section of the particle, the difference between the average major diameter and the average minor diameter is less than 20%. The surfaces of the microspheres of the present invention appear smooth under magnification of up to 1000 times. The microspheres of the present invention may comprise, in addition to the particles, other materials as described and defined herein.

As used herein, "cell adhesion promoter" in the present invention means any material that, because of their presence in or association with the microspheres, promotes or enhances the adhesiveness of cells to the surface of the microspheres. These materials are often proteins that are associated with the surface of the microspheres through covalent bonds or in an interpenetrated polymeric manner.

As used herein, "therapeutic agent" in the present invention refers to any substance that provides therapeutic effects to the process of angiogenesis-dependent diseases or biological or physiological responses to the angiogenesis-dependent diseases. An example of a therapeutic agent is an anti-inflammation agent that prevents or reduces the effect of inflammations associated with angiogenesis-dependent diseases.

As used herein, "chemical modification" in the present invention means the changes of chemical properties and characteristics of the microspheres, either during their production process or by way of mixing or contacting them with various agents or tissues, such that the microspheres have the ability to perform, in addition to tumor embolization, other functions once injected into the body.

As used herein, "stabilizing material" or "stabilizing compound" refers to any material which is capable of improving the stability of compositions, prodrugs, targeting ligands and/or other bioactive therapeutic factors described herein, including, for example, mixtures, suspensions, emulsions, dispersions, vesicles, or the like. Encompassed in the definition of "stabilizing material" are certain of the present bioactive therapeutic factors and prodrugs. Also encompassed within the definition of "stabilizing material" are certain of the present transfection agents. The improved stability involves, for example, the maintenance of a relatively balanced condition, and may be exemplified, for example, by increased resistance of the composition against destruction, decomposition, degradation, and the like. For example, a dangling cationic head in a transfection agent reduces the transfection efficiency, as seen with such compounds as $C_{12}GluPhC_nN^+$ and $C_{14}GluPhC_nN^+$ whereas compounds such as DOTB/DOSC which have the shortest spacers lead to the highest surface charge density and the best transfection efficiency.

In the case of preferred embodiments involving microspheres with bioactive therapeutic factors, prodrugs and/or other bioactive agents, the stabilizing compounds may serve to either form the microspheres or stabilize the microspheres, in either way serving to minimize or substantially (including completely) prevent the release of certain bioactive therapeutic factors, prodrugs and/or bioactive agents from the microspheres until said release is desired. The term "substantially," as used in the present context of preventing release of bioactive therapeutic factors, prodrugs and/or bioactive agents from the microspheres, means greater than about 50% is maintained associated on the surface or contained within the microspheres until release is desired, and preferably greater than about 60%, more preferably greater than about 70%, even more preferably greater than about 80%, still even more preferably greater than about 90%, is maintained associated on the surface or alternatively, in the case of therapeutic drug formulations, contained within the microspheres until release is desired. In particularly preferred embodiments, greater than about 95% of the bioactive therapeutic factors, prodrugs and/or bioactive agents are maintained associated on the surface or alternatively, in the case of therapeutic drug formulations, contained within the microspheres until release is desired. The bioactive therapeutic factors, prodrugs and/or bioactive agents may also be completely maintained associated on the surface or contained within the microspheres (i.e., about 100% is maintained associated on the surface or contained within the microspheres), until release is desired.

Exemplary stabilizing materials include, for example, lipids, proteins, polymers, carbohydrates and surfactants. The resulting mixture, suspension, emulsion or the like may comprise walls (i.e., films, membranes and the like) around the bioactive therapeutic factor, or bioactive agent, or may be substantially devoid of walls or membranes, if desired. The stabilizing material may, if desired, form droplets. The stabilizing material may also comprise salts and/or sugars. In certain embodiments, the stabilizing materials may be substantially (including completely) cross-linked. The stabilizing material may have a neutral, positive or negative charge.

As used herein, "cross-link," "cross-linked" and "cross-linking" generally refer to the linking of two or more stabilizing materials, including lipid, protein, polymer, carbohydrate, surfactant stabilizing materials, bioactive therapeutic factor and/or bioactive agents, by one or more bridges. The bridges may be composed of one or more elements, groups, or compounds, and generally serve to join an atom from a first stabilizing material molecule to an atom of a second stabilizing material molecule. The cross-link bridges may involve covalent and/or non-covalent associations. Any of a variety of elements, groups, and/or compounds may form the bridges in the cross-links, and the stabilizing materials may be cross-linked naturally or through synthetic means. For example, cross-linking may occur in nature in material formulated from peptide chains which are joined by disulfide bonds of cystine residues, as in keratins, insulins and other proteins. Alternatively, cross-linking may be effected by suitable chemical modification, such as, for example, by combining a compound, such as a stabilizing material, and a chemical substance that may serve as a cross-linking agent, which may cause to react by, for example, exposure to heat, high-energy radiation, and the like. Examples include cross-linking by sulfur to form disulfide linkages, cross-linking using organic peroxides, cross-linking of unsaturated materials by means of high-energy radiation, cross-linking with dimethylol carbamate, and the like. If desired, the stabilizing compounds, bioactive therapeutic factor and/or bioactive agents may be substantially cross-linked.

As used herein, the term "substantially" means that greater than about 50% of the stabilizing compounds contain cross-linking bridges. If desired, greater than about 60%, 70%, 80%, 90%, 95% or even 100% of the stabilizing compounds contain such cross-linking bridges. Alternatively, the stabilizing materials may be non-cross-linked, i.e., such that greater than about 50% of the stabilizing compounds are devoid of cross-linking bridges, and if desired, greater than about 60%, 70%, 80%, 90%, 95% or even 100% of the stabilizing compounds are devoid of cross-linking bridges.

As used herein, "associated" refers to an attachment between the bioactive therapeutic agent, the transfection agent, and the microsphere of the invention. Such an association, in the case of the bioactive therapeutic agent and the transfection agent may or may not result in the formation of a complex. Such an association is meant to include, without limitation, those associations which are covalent, non-covalent, as well as ionic interactions, electrostatic interactions, Van der Waal's forces, hydrogen bonds, hydrophilic interactions, and hydrophobic interactions, each of which are defined further herein below.

As used herein, "covalent association" refers to an intermolecular association or bond which involves the sharing of electrons in the bonding orbitals of two atoms.

As used herein, "non-covalent association" refers to intermolecular interaction among two or more separate molecules which does not involve a covalent bond. Intermolecular interaction is dependent upon a variety of factors, including, for example, the polarity of the involved molecules, and the charge (positive or negative), if any, of the involved molecules. Non-covalent associations are selected from ionic interactions, dipole-dipole interactions, Van der Waal's forces, and combinations thereof.

As used herein, "ionic interaction" or "electrostatic interaction" refers to an intermolecular interaction among two or more molecules, each of which is positively or negatively charged. Thus, for example, "ionic interaction" or "electrostatic interaction" refers to the attraction between a first, positively charged molecule and a second, negatively charged molecule. Ionic or electrostatic interactions include, for example, the attraction between a negatively charged stabilizing material, for example, genetic material, and a positively charged lipid, for example, a cationic lipid, such as lauryltrimethylammonium bromide.

As used herein, "Van der Waal's forces" refer to the attractive forces between non-polar molecules that are accounted for by quantum mechanics. Van der Waal's forces are generally associated with momentary dipole moments which are induced by neighboring molecules and which involve changes in electron distribution.

As used herein, "hydrogen bond" refers to an attractive force, or bridge, which may occur between a hydrogen atom which is bonded covalently to an electronegative atom, for example, oxygen, sulfur, or nitrogen, and another electronegative atom. The hydrogen bond may occur between a hydrogen atom in a first molecule and an electronegative atom in a second molecule (intermolecular hydrogen bonding). Also, the hydrogen bond may occur between a hydrogen atom and an electronegative atom which are both contained in a single molecule (intramolecular hydrogen bonding).

As used herein, "hydrophilic interaction" refers to molecules or portions of molecules which may substantially bind with, absorb and/or dissolve in water. This may result in swelling and/or the formation of reversible gels.

As used herein, "hydrophobic interaction" refers to molecules or portions of molecules which do not substantially bind with, absorb and/or dissolve in water.

For clarity of disclosure, and not by way of limitation, the detailed description of the present invention is divided into the subsections which follow.

The present invention provides safe and effective methods of embolizing gene therapy, which methods are useful for the treatment of cancer and various other angiogenesis-dependent diseases. Such methods of embolizing gene therapy are thus beneficial for physicians and/or surgeons, including, without limitation, interventional radiologists. The methods and compositions of the present invention may be used by surgeons either prior to, during or after surgery.

Briefly, in gene therapy, genes are delivered into the patient's cells as molecules of DNA or RNA. The genes form part of expression construct-cassettes of nucleic acids which include the gene of interest and a promoter/enhancer element which directs high level expression of the gene within the target cells. The DNA is transcribed by enzymes within the cell into RNA messenger molecule, which form the template for translating the gene sequence into the protein product. This protein then supplies a function within the target cell or environmental tissue either to correct a cellular defect or to kill cells such as tumor cells.

Thus, gene and cell therapy consists of correcting a deficiency or an abnormality (mutation, aberrant expression and the like) or in ensuring the expression of a protein of therapeutic interest by the introduction of a genetic information into the cell or the affected organ. This genetic information can be introduced either in vitro into a cell extracted from the organ, the modified cell then being reintroduced into the body, or directly in vivo into the appropriate tissue. Various techniques have been described for the transfer of this genetic information, amongst which are various transfection techniques involving complexes of DNA and DEAE-dextran (Pagano et al., *J. Virol.* 1 (1967) 891), of DNA and nuclear proteins (Kaneda et al, *Science* 243 (1989) 375), of DNA and lipids (Feigner et al., *PNAS* 84 (1987) 7413), of DNA and polylysine, the use of liposomes (Fraley et al., *J. Biol. Chem.* 255 (1980) 10431) and the like.

Embolization is a partial or total occlusion of vessels where the blood is flushing. Therapeutic embolization is a procedure that allows to occlude arteries or veins either to correct a dysfunction such as an arteriovenous malformation or to stop the blood flow with the goal to stop supplying essential element to a solid tumor/cancer growth. Most generally therapeutic embolization is a "passive" operation in the sense that no active molecules are carried and/or delivered where the embolic material is deposited.

The present invention is directed to an "active" embolization associating the reduction of blood flow with the localized delivery of a transfectable genetic material both of which act with the same objective, the reduction or the elimination of cancer cells.

Within one aspect of the present invention, compositions are provided comprising (a) a bioactive therapeutic factor, (b) a microsphere carrier, and (c) a transfection agent. In a preferred embodiment, the invention provides methods of gene therapy by administrating an injectable composition comprising (a) a bioactive therapeutic factor, (b) a microsphere carrier, and (c) a transfection agent to a mammal in need of treatment for cancer and various other angiogenesis-dependent diseases.

In another preferred embodiment, the invention provides methods of gene therapy by administrating an injectable composition comprising (a) a bioactive therapeutic factor, (b) a microsphere carrier, and (c) a transfection agent to a mammal in need of treatment for cancer and various other angiogenesis-dependent diseases, wherein said injectable composition is administered directly into the tumor or diseased tissue via a suitable gauged needle.

In yet another preferred embodiment, the invention provides methods of gene therapy by administrating an injectable composition comprising (a) a bioactive therapeutic factor, (b) a microsphere carrier, and (c) a transfection agent to a mammal in need of treatment for cancer and various other angiogenesis-dependent diseases, wherein said injectable composition is delivered to the tumor or diseased tissue by injection into the vascular system.

Within another aspect of the present invention, methods are provided for treating a tumor excision site, comprising administering a composition comprising an anti-neoplastic drug such as for example, without limitation, taxol, doxorubicin, cisplatin, paclitaxel, to the resection margin of a tumor subsequent to excision, such that the local recurrence of cancer and the formation of new blood vessels at the site is inhibited.

The polymeric carriers or preferably microspheres of the present invention also can be chemically modified to so contain therapeutic effects, vascularization effects, anti-vascularization effects, visualization properties, or combinations thereof. In one embodiment, the chemical modification of the microspheres of the present invention is made possible by the fact that the microspheres comprise particles made of polymers that are crosslinked so that they can contain chemicals within their structures that possess various properties and that they possess unique characteristics associated with surface covalent bonds. The chemical modification of the microspheres of the present invention may also occur through the interactions between the microspheres and the neighboring cells and tissue after the administration.

The methods of the present invention have the following advantages: (1) the injected materials are not easily displaced within the tissues in which they were originally injected, thus the intended gene therapy is achieved without repeated administration or causing adverse effects to the patient, (2) the injected materials are not readily digested, displaced, or eliminated either biochemically or through the immune or lymphatic system, thus the method is more effective and longer lasting, (3) the materials are of sufficient size to be injected through 18 to 26 gauge needles or 30 gauge or smaller needles, thus the method is more accurate, efficacious and less intrusive to the patient, (4) the injected particles are flexible, but not fragile, facilitating easy injection without being broken, thus providing easy and safe injection, and (5) the injected particles are not irregularly shaped and do not clump together, also providing easy and accurate injection. These benefits, whether alone or in combination, enhance the effectiveness of the treatment and are safe, more convenient and comfortable for patients.

4.1 Polymeric Material 4.1.1 Microparticles

For the delivery of the polynucleotides or other genetic materials of the present invention, any polymeric material may be used which is capable of associating with the polynucleotide or other genetic material and the transfection agent and which can target the site of action. In a preferred embodiment, the material should carry the polynucleotides or other genetic materials and embolize. Preferably, a microparticle is used in the present invention, most preferably a microsphere.

A wide variety of polymeric carriers may be utilized in the present invention, representative examples of which include, without limitation, poly (ethylene-vinyl acetate) (40% cross-linked), poly (D,L-lactic acid) oligomers and polymers, poly (L-lactic acid) oligomers and polymers, poly (glycolic acid), copolymers of lactic acid and glycolic acid, poly (caprolactone), poly (valerolactone), poly (anhydrides), copolymers of poly (caprolactone) or poly (lactic acid) with polyethylene glycol, polysaccharides, silicone, and blends thereof.

4.1.2 Microspheres

For the drug delivery aspect of the invention, the preferred polymeric material is the microsphere. In the drug delivery embodiment, the use of a transfection agent is optional.

Preferably the microbeads or microspheres (collectively referred to herein as microspheres) for use in the present invention are based on a biocompatible, hydrophilic, substantially spherical, and non-toxic polymers. The microspheres are injectable through a needle of 18 gauge or smaller and are not capable of being eliminated by the immune or lymphatic system. The polymers may preferably be coated with agents which promote cell adhesion. Living cells may also attach to the microspheres forming layered cells therein which link with surrounding tissues to enhance long term stability of the beads.

The microspheres of the present invention comprise elastomers, preferably elastomers selected from the group consisting of acrylic polymers, vinyl alcohol polymers, acrylate polymers, polysaccharides, silicones, or mixtures thereof. More preferably, the hydrophilic copolymers usable for this application are those of the acrylic family such as polyacrylamides and their derivatives, polyacrylates and their derivatives as well as polyallyl and polyvinyl compounds. In another embodiment, microspheres of the present invention may also be based upon the combination of polyvinyl acetate in conjunction with a cationic hydrophobic polymer. All of these polymers are cross-linked so as to be stable and non-resorbable, and can contain within their structure other chemicals displaying particular properties, such as chemotactic effects, promotion of cell adhesion to cells or tissues.

Microspheres intended to be implanted, preferably through injection, in various locations of the body according to the present invention are composed of a non-resorbable hydrophilic polymer containing the appropriate material for cell adhesion, and may additionally contain radiopaque molecules or other marking agents, to facilitate localization by radiology prior to or during intervention.

The microspheres for use in the present invention are non-toxic to tissues and cells, biocompatible, and adhesive to various cells and tissues at the site of implantation by means of the cell growth they promote. In addition, these microspheres are non-resorbable and non-biodegradable, and thus are stable, durable, and will maintain their general shape and position once implanted at a desired site. In an alternative embodiment, the microspheres of the present invention are resorbable and thus biodegradable. Such resorbable and biodegradable microspheres are based upon, for example, without limitation, polysaccharide and polysaccharide derivatives.

In general, microspheres for use in the present invention may have any shape, with microspheres which are substantially spherical in shape being preferred. Microspheres for use in the present invention may have diameters ranging between about 10 µm to about 2000 µm. Preferably, microspheres for use in the present invention which have cells adhered to the surface thereof will have diameters ranging between 40 µm and 1000 µm.

The elastic microspheres of the present invention are preferably capable of being injected through needles of 18 gauge or smaller and are eliminated through macrophages or other elements of the immune system or the lymphatic system. In such cases, the preferred average diameters of the microspheres are from about 40 µm to about 400 µm and, more preferably, from about 50 to about 200 µm. In a most preferred embodiment, the average diameters of the injectable microspheres range from about 70 to about 120 µm.

In another aspect of the invention a subset of the microspheres for use in the present invention are based on non-toxic, biocompatible, swellable, hydrophilic, and substantially spherical particles which comprise various polymers. The swellable microspheres are crosslinked polymers that are high water absorbing and, thus, capable of swelling upon contacting with aqueous medium in certain conditions. As understood by a person skilled in the art, the degree of swelling of crosslinked polymers generally depends on the properties of the polymeric materials and the degree of crosslinking. Properties, such as salt and ionic concentration and level of pH, of the solvent in which the microspheres are suspended or with which the microspheres are contacting also affect the degree of swelling.

By carefully controlling the size and the degree of swelling of certain crosslinked and swellable polymers, embolization and gene delivery can be achieved using these microspheres. According to the invention, polymeric materials having high water absorbing ability are first chosen. The swellability of these polymers can be further manipulated by controlling the degree of crosslinking, which, as known to a skilled artisan, can be achieved either chemically or through radiation.

More importantly, the swelling of the microspheres comprising these polymers can be further controlled by controlling the solvent in which the microspheres are suspended. This is achieved through two steps as disclosed herein. First, the size of the microspheres before injection are carefully controlled by using appropriate solvents, salt concentration and pH level according to the specific microspheres used. The microspheres before injection may either remain in their original size or swell to certain degree due to their contact with the solvent. The pre-injection swelling is controlled so that the microspheres are easily injectable through 30 gauge or smaller needles. Second, after injection and upon contacting with tissues at injection site, the microspheres may further swell into predetermined size or retain their pre-injection size, either of which size will allow the microspheres to be secured at the site of injection and achieve desired embolization gene therapy effect. The degree of pre-injection swelling, and thus the after injection swelling, is determined by the particular microspheres used and the nature and location of the skin deficiencies being treated.

Microspheres for use in the present invention have diameters ranging from about 10 to about 400 µm before swelling. Preferably, before swelling, the diameters of the microspheres are from about 10 to about 200 µm and, most preferably, from about 10 to about 120 µm. After injection and swelling, the microspheres have average diameters larger than about 40 µm, preferably larger than about 50 µm and, more preferably, larger than about 70 µm. The microspheres of the present invention are capable of swelling to about 15 times of their original sizes. The full swollen size of the microspheres after injection are controlled, by various means discussed above, so that they are secured at the site of injection while not causing any potential injuries to the tissues. Further, the full swollen sizes of the microspheres after injection are predetermined based on factors such as the physiological conditions of the injection site, the original microspheres sizes, the solvent used and the pre-injection swelling of the microspheres. Thus, a specific injection plan can be designed according to the particular embolotherapy gene therapy need of the case. These sizes and properties of the microspheres are advantageous in that they enable the microspheres to be easily injectable through needles of 30 gauge or smaller, yet the microspheres are large enough so that they will be secured at the site of injection and will not be digested or eliminated by macrophage or other elements of the immune system.

Possible variations of the microspheres of the present invention include replacing the microspheres with any biocompatible, non-toxic non-resorbable polymeric particles, membrane, fibers or other solid substrates treated with an agent promoting cell adhesion. The invention also encompasses the use of embolic material which can be a liquid gellable solution as disclosed in U.S. Pat. No. 5,925,683, the entire contents of which are incorporated herein by reference. The invention also includes linear soluble polymers which, after injection, cross-link in situ to constitute a solid, cell adhesion promoting filling agent. Preparation and/or injection of empty microspheres (microbubbles) that are prepared in advance or are generated in place via the use of appropriate catheters, are also contemplated in this invention.

The microspheres, or other solid substrates, for use in the present invention are flexible, such that they can easily pass into and through injection devices and small catheters without being permanently altered, but the microspheres are also resistant to the muscle contraction stress generated during and after the implantation process. They are also thermally stable which allows for easy, convenient sterilization, and frozen storage.

The microspheres, or other solid substrates, for use in the present invention are also stable in suspension which allows the microspheres or other solid substrates to be formulated and stored in suspension and injected with different liquids. More specifically, the hydrophilic nature of the microspheres permits placing them in suspension, and in particular, in the form of sterile and pyrogenic (pyrogen-free) injectable solutions, while avoiding the formation of aggregates or adhesion to the walls of storage containers and implantation devices, such as catheters, syringes, needles, and the like.

In one embodiment, the preferred microspheres of the present invention are both hydrophilic and cationic. The microspheres preferably comprise a copolymer of a neutral hydrophilic monomer, a difunctional monomer, one or more monomers having a cationic charge, and optionally, a functionalized monomer capable of rendering the microsphere detectable. The microspheres may also comprise one or more cell adhesion promoters and a marking agent. The copolymer is preferably a hydrophilic acrylic copolymer which comprises in copolymerized form about 25 to about 98% neutral hydrophilic acrylic monomer by weight, about 2 to about 50% difunctional monomer by weight and about 0 to about 50% by weight of one or more monomers having a cationic charge. By way of example, the copolymers described in French Patent 2,378,808, which is incorporated herein by reference, can be used in accordance with this invention to prepare the base microsphere copolymer. As hydrophilic acrylic monomer, acrylamide and its derivatives, methacrylamide and its derivatives or hydroxymethylmethacrylate can be used. Examples of difunctional monomer, include, but are not limited to, the N,N'-methylene-bis-acrylamide, N',N'-diallyltartiamide or glyoxal-bis-acrylamide. Further, the monomer having a cationic charge, includes, but is not limited to, those carrying a tertiary or quaternary amine function, preferably diethylaminoethyl acrylamide, methacrylamidopropyl trimethylammonium or acrylamidoethyl triethylammonium. In a particularly preferred embodiment, a copolymer comprising about 25 to about 98% methacrylamide by weight, about 2 to about 50% N,N-methylene-bis-acrylamide by weight is used.

In another related aspect of the present invention, the hydrophobicity or ionic character of the embolic material can be modified as deemed necessary by introducing for example, without limitation, hydrocarbon chains and/or hydrophilic ionizable chemical groups. Such modifications of the embolic material result in an increased adsorption strength between the bioactive therapeutic factor and the transfecting agent, which is sufficient to modulate the time span for the delivery of bioactive therapeutic factor. Such modulation of the adsorption strength between the bioactive therapeutic factor and the transfecting agent can also be used to control the absolute amount of bioactive therapeutic factor associated with the embolic material.

In one particularly advantageous embodiment of the invention, it is possible to increase the stability of the microspheres by reticulating the adhesion agent. By way of example, in the case of gelatin, the reticulating agent can be chosen among the difunctional chemical agents reacting on the gelatin amines (e.g., glutaraldehyde, formaldehyde, glyoxal, and the like).

Another embodiment of the invention is to have the microsphere visible in the light and within the body. For example, it is also possible to mark the microspheres after their synthesis. This can be done, for example, by grafting of fluorescent markers derivatives (including, for example, fluorescein isothiocyanate (FITC), rhodamine isothiocyanate (RITC) and the like). The functionalized monomer is generally obtained by chemical coupling of the monomer with a marker, which can be: a chemical dye, such as Cibacron Blue or Procion Red HE-3B, making possible a direct visualization of the microspheres (Boschetti, *J. Biochem-Biophys. Meth.*, 19:21-36 (1989)). Examples of functionalized monomer usable for this type of marking N-acryloyl hexamethylene Cibacrone Blue or N-acryloyl hexamethylene Procion Red HE-3B; a magnetic resonance imaging agent (erbium, gadolinium or magnetite); a contrasting agent, such as barium or iodine salts, (including, for example, acylamino-e-propionamido)-3-triiodo-2,4,6-benzoic acid, which can be prepared under the conditions described by Boschetti et al. (*Bull. Soc. Chim.*, No. 4 France, (1986)). In the case of barium or magnetite salts, they can be directly introduced in powdered form in the initial monomer solution.

Various types of cell adhesion promoters well known in the art may be used in the present invention. In particular, cell adhesion promoters can be selected from collagen, gelatin, glucosaminoglycans, fibronectins, lectins, polycations (such polylysine, chitosan and the like), or any other natural or synthetic biological cell adhesion agent.

Preferably, the cell adhesion promoter is present in the microsphere, or other solid substrate, in an amount between about 0.1 to 1 g per ml of settled microspheres.

Microspheres are prepared by suspension polymerization, drop-by-drop polymerization or any other method known to the skilled artisan. The mode of microsphere preparation selected will usually depend upon the desired characteristics, such as microsphere diameter and chemical composition, for the resulting microspheres. The microspheres of the present invention can be made by standard methods of polymerization described in the art (see, e.g., E. Boschetti, *Microspheres for Biochromatography and Biomedical Applications. Part I, Preparation of Microbeads* In: Microspheres, Microencapsulation and Liposomes, John Wiley & Sons, Arshady R., Ed., vol. 2, p. 171-189 (1999), which is incorporated herein by reference). Microspheres are prepared starting from an aqueous solution of monomers containing adhesion agents such as collagen (gelatin is a denatured collagen). The solution is then mixed with a non-aqueous-compatible solvent to create a suspension of droplets, which are then turned into solid gel by polymerization of monomers by means of appropriate catalysts. Microspheres are then collected by filtration or centrifugation and washed.

Cell adhesion promoters or marking agents are introduced on microspheres by chemical coupling procedures well known in affinity chromatography, referred to by the term "ligand immobilization". Another method of introduction is by diffusion within the gel network that constitutes the microsphere and then trapping the diffused molecules in place by precipitation or chemical cross-linking.

The microspheres of the invention can also be obtained by standard methods of polymerization described in the art such as French Patent 2,378,808, U.S. Pat. Nos. 5,648,100, 5,635, 215 and 5,648,100, each of which is incorporated herein by reference. In general, the polymerization of monomers in solution is carried out at a temperature ranging between about 0° C. and about 100° C. and between about 40° C. and about 60° C., in the presence of a polymerization reaction initiator.

The polymerization initiator is advantageously chosen among the redox systems. Notably, it is possible to use combinations of an alkali metal persulfate with N,N,N,'N'-tetramethylethylenediamine or with dimethylaminopropionitrile, organic peroxides such as benzoyl peroxides or even 2,2'-azobis-isobutyronitrile. The quantity of initiator used is adapted by one skilled in the art to the quantity of monomers and the rate of polymerization sought. Polymerization can be carried out in mass or in emulsion.

In the case of a mass polymerization, the aqueous solution containing the different dissolved constituents and the initiator undergoes polymerization in an homogeneous medium. This makes it possible to access a lump of aqueous gel which can then be separated into microspheres, by passing, for example, through the mesh of a screen.

Emulsion or suspension polymerization is the preferred method of preparation, since it makes it possible to access directly microspheres of a desired size. It can be conducted as follows: The aqueous solution containing the different dissolved constituents (e.g., different monomers, cell adhesion agent), is mixed by stirring, with a liquid organic phase which is not miscible in water, and optionally in the presence of an emulsifier. The rate of stirring is adjusted so as to obtain an aqueous phase emulsion in the organic phase forming drops of desired diameter. Polymerization is then started off by addition of the initiator. It is accompanied by an exothermic reaction and its development can then be followed by measuring the temperature of the reaction medium.

It is possible to use as organic phase vegetable or mineral oils, certain petroleum distillation products, chlorinated hydrocarbons or a mixture of these different solutions. Furthermore, when the polymerization initiator includes several components (redox system), it is possible to add one of them in the aqueous phase before emulsification.

The microspheres thus obtained can then be recovered by cooling, decanting and filtration. They are then separated by size category and washed to eliminate any trace of secondary product.

The polymerization stage can be followed by a stage of reticulation of the cell adhesion agent and possibly by a marking agent stage in the case of microspheres rendered identifiable by grafting after synthesis.

4.2 Bioactive Therapeutic Factors

The bioactive therapeutic factors of the present invention comprise at least one or more of the following: Antineoplastic agents, anti-angiogenic agents, hormones and steroids, vitamins, peptides and peptide analogs, antibodies or fragments thereof, anti-mitotic factors, vaccines, enzymes, anti-allergenic agents, circulatory drugs, anti-tubercular agents, anti-viral agents, anti-anginal agents, anti-bacterial agents, and anti-fungal agents, anti-inflammatory agents, anti-protozoan agents, anti-rheumatic agents, narcotics, cardiac glycoside agents, sedatives, local anesthetic agents, anti-histamine drugs, radiosensitive agents, general anesthetic agents, or combinations thereof.

4.3 Bioactive Therapeutic Factors for Use in Gene Therapy

For the polynucleotide-based embolotherapy gene therapy, the polynucleotide may encode any of the bioactive therapeutic factors of the present invention, wherein the polynucleotide is associated with a transfection agent of the present invention. Genetic materials encoding the bioactive therapeutic factors of the present invention, include, for example, without limitation, nucleic acids, polynucleotides, RNA and DNA, of either natural or synthetic origin, including recombinant RNA and DNA and antisense RNA and DNA; hammerhead RNA, ribozymes, antigen nucleic acids, both single and double stranded RNA and DNA and analogs thereof, such as phosphorothioate and phosphorodithioate oligodeoxynucleotides. Types of genetic material that may be used include, for example, genes carried on expression vectors such as plasmids, phagemids, cosmids, yeast artificial chromosomes (YACs), and defective or "helper" viruses, as well as virus-like particles carrying the genetic material. Such polynucleotides may also be used in combination with other elements such as, for example, without limitation, tissue specific enhancers, nuclear localization signals, etc.

Additionally, the genetic material may be combined, for example, with proteins or other polymers. For example, in one embodiment, the invention also provides for the use of targeting polyclonal and monoclonal antibodies in conjunction with the polymeric material carrier, the bioactive therapeutic factor and the transfection agent. Some examples of genetic therapeutics that may be applied using the microspheres of the present invention include DNA encoding at least a portion of an HLA gene, DNA encoding at least a portion of dystrophin, DNA encoding at least a portion of the cystic fibrosis transmembrane regulator (CFTR), DNA encoding at least a portion of IL-2, DNA encoding at least a portion of TNF, an antisense oligonucleotide capable of binding the DNA encoding at least a portion of Ras. DNA encoding certain proteins may be used in the treatment of many different types of diseases. For example, tumor necrosis factor and/or interleukin-2 may be provided to treat advanced cancers; HDL receptor may be provided to treat liver disease; thymidine kinase may be provided to treat ovarian cancer, brain tumors, or HIV infection; HLA-B7 may be provided to treat malignant melanoma; interleukin-2 may be provided to treat neuroblastoma, malignant melanoma, or kidney cancer; interleukin-4 may be provided to treat cancer; HIV env may be provided to treat HIV infection; antisense ras/p53 may be provided to treat lung cancer; adenosine deaminase may be provided to treat ADA deficiency; and Factor VIII may be provided to treat Hemophilia B. See, for example, Science 258, 744-746.

4.4 Bioactive Therapeutic Factors for Use in Drug Therapy

For the drug-based embolotherapy aspect of the invention, the bioactive therapeutic factors comprise one or more of the following agents associated with a microsphere of the invention.

Antineoplastic agents, include, for example, without limitation, platinum compounds (e.g., spiroplatin, cisplatin, and carboplatin), adriamycin, mitomycin c, ansamitocin, bleomycin, bleomycin sulfate, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride, dactinomycin (actinomycin D), daunorubicin hydrochloride, doxorubicin hydrochloride, taxol, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase), Erwina asparaginase, etoposide (VP-16), interferon α-2a, interferon α-2b, teniposide (VM-26), vinblastine sulfate (VLB), vincristine sulfate, methotrexate, and carzelesin.

Blood products, include, for example, without limitation, erythropoietin, parenteral iron, hemin, and hematoporphyrins and their derivatives.

Biological response modifiers, include, for example, without limitation, muramyldipeptide, muramyltripeptide, lymphokines (e.g., bacterial endotoxin such as lipopolysaccharide, macrophage activation factor), sub-units of bacteria (such as Mycobacteria, Corynebacteria), the synthetic dipeptide, N-acetyl-muramyl-L-alanyl-D isoglutamine, and prostaglandins.

Anti-fungal agents, include, for example, without limitation, ketoconazole, nystatin, griseofulvin, flucytosine (5-fc), miconazole, amphotericin B, ricin, and .beta.-lactam antibiotics (e.g., sulfazecin).

Hormones and steroids, include, for example, without limitation, growth hormone, melanocyte stimulating hormone, adrenocortiotropic hormone, dexamethasone, dexamethasone acetate, dexamethasone sodium phosphate, cortisone, cortisone acetate, hydrocortisone, hydrocortisone acetate, hydrocortisone cypionate, hydrocortisone sodium phosphate, hydrocortisone sodium succinate, prednisone, prednisolone, prednisolone acetate, prednisolone sodium phosphate, prednisolone tebutate, prednisolone pivalate, triamcinolone, triamcinolone acetonide, triamcinolone hexacetonide, triamcinolone diacetate, methylprednisolone, methylprednisolone acetate, methylprednisolone sodium succinate, flunsolide, beclomethasone dipropionate, betamethasone sodium phosphate, betamethasone, vetamethasone disodium phosphate, vetamethasone sodium phosphate, betamethasone acetate, betamethasone disodium phosphate, chloroprednisone acetate, corticosterone, desoxycorticosterone, desoxycorticosterone acetate, desoxycorticosterone pivalate, desoximethasone, estradiol, fludrocortisone, fludrocortisone acetate, dichlorisone acetate, fluorohydrocortisone, fluorometholone, fluprednisolone, paramethasone, paramethasone acetate, androsterone, fluoxymesterone, aldosterone, methandrostenolone, methylandrostenediol, methyl testosterone, norethandrolone, testosterone, testosterone enanthate, testosterone propionate, equilenin, equilin, estradiol benzoate, estradiol dipropionate, estriol, estrone, estrone benzoate, acetoxypregnenolone, anagestone acetate, chlormadinone acetate, flurogestone acetate, hydroxymethylprogesterone, hydroxymethylprogesterone acetate, hydroxyprogesterone, hydroxyprogesterone acetate, hydroxyprogesterone caproate, melengestrol acetate, normethisterone, pregnenolone, progesterone, ethynyl estradiol, mestranol, dimethisterone, ethisterone, ethynodiol diacetate, norethindrone, norethindrone acetate, norethisterone, fluocinolone acetonide, flurandrenolone, flunisolide, hydrocortisone sodium succinate, methylprednisolone sodium succinate, prednisolone phosphate sodium, triamcinolone acetonide, hydroxydione sodium spironolactone, oxandrolone, oxymetholone, prometholone, testosterone cypionate, testosterone phenylacetate, estradiol cypionate, and norethynodrel.

Vitamins, include, for example, without limitation, cyanocobalamin neinoic acid, retinoids and derivatives thereof such as retinol palmitate, alpha.-tocopherol, naphthoquinone, cholecalciferol, folic acid and tetrahydrofolate.

Peptides and peptide analogs, include, for example, without limitation, manganese super oxide dismutase, tissue plasminogen activator (t-PA), glutathione, insulin, dopamine, peptide ligands containing RGD, AGD, RGE, KGD, KGE or KQAGDV (peptides with affinity for the GPIIBIIIa receptor), opiate peptides, enkephalins, endorphins and their analogs, human chorionic gonadotropin (HCG), corticotropin release factor (CRF), cholecystokinins and their analogs, bradykinins and their analogs and promoters and inhibitors, elastins, vasopressins, pepsins, glucagon, substance P, integrins, captopril, enalapril, lisinopril and other ACE inhibitors, adrenocorticotropic hormone (ACTH), oxytocin, calcitonins, IgG or fragments thereof, IgA or fragments thereof, IgM or fragments thereof, ligands for Effector Cell Protease Receptors (all subtypes), thrombin, streptokinase, urokinase, t-PA and all active fragments or analogs, Protein Kinase C and its binding ligands, interferons (.alpha.-interferon, .beta.-interferon, .gamma.-interferon), colony stimulating factors (CSF), granulocyte colony stimulating factors (GCSF), granulocyte-macrophage colony stimulating factors (GM-CSF), tumor necrosis factors (TNF), nerve growth factors (NGF), platelet derived growth factors, lymphotoxin, epidermal growth factors, fibroblast growth factors, vascular endothelial cell growth factors, erythropoietin, transforming growth factors, oncostatin M, interleukins (1, 2, 3, 4, 5, 6, 7, 8, 9, 10, 11 and 12), metalloprotein kinase ligands, collagenases and agonists and antagonists.

As used herein, antibodies include, for example, without limitation, substantially purified antibodies or fragments thereof, including non-human antibodies or fragments thereof. In various embodiments, the substantially purified antibodies of the invention, or fragments thereof, can be human, non-human, chimeric and/or humanized antibodies. Such non-human antibodies can be goat, mouse, sheep, horse, chicken, rabbit, or rat antibodies. Alternatively, the non-human antibodies of the invention can be chimeric and/or humanized antibodies. Completely human antibodies are particularly desirable for therapeutic treatment of human patients. A chimeric antibody is a molecule in which different portions are derived from different animal species, such as those having a variable region derived from a murine mAb and a human immunoglobulin constant region (Cabilly et al., U.S. Pat. No. 4,816,567; and Boss et al., U.S. Pat. No. 4,816,397, which are incorporated herein by reference in their entirety.). In addition, the non-human antibodies contemplated within the scope of the invention can be polyclonal antibodies or monoclonal antibodies. Any of the antibodies of the invention can be conjugated to a therapeutic moiety or to a detectable substance. Non-limiting examples of detectable substances that can be conjugated to the antibodies of the invention are an enzyme, a prosthetic group, a fluorescent material, a luminescent material, a bioluminescent material, and a radioactive material.

The invention provides for the use of targeting polyclonal and monoclonal antibodies in conjunction with the polymeric material carrier, the bioactive therapeutic factor and the transfection agent. Such antibodies are useful in the methods of the invention and enable the targeted delivery of the polymeric material and the bioactive therapeutic factor linked to the transfection agent to the site of action. The term "monoclonal antibody" or "monoclonal antibody composition", as used herein, refers to a population of antibody molecules that contain only one species of an antigen binding site capable of immunoreacting with a particular epitope. Polyclonal antibodies can be prepared as described above by immunizing a suitable subject with a polypeptide of the invention as an immunogen. Preferred polyclonal antibody compositions are ones that have been selected for antibodies directed against a polypeptide or polypeptides of, for example, a receptor on the surface of a cancer cell of a tumor to be treated by the compositions of the present invention.

Anti-mitotic factors include, without limitation, estramustine and its phosphorylated derivative, estramustine-phosphate, doxorubicin, amphethinile, combretastatin A4, and colchicine.

Vaccines include, for example, without limitation, pneumococcus vaccine, pciliomyelitis vaccine, anthrax vaccine, tuberculosis (BCG) vaccine, hepatitis A vaccine, cholera vaccine, meningococcus A, C, Y vaccines, W135 vaccine, plague vaccine, rabies (human diploid) vaccine, yellow fever vaccine, Japanese encephalitis vaccine, typhoid (phenol and heat-killed) vaccine, hepatitis B vaccine, diptheria vaccine, tetanus vaccine, pertussis vaccine, *H. influenzae* type b vaccine, polio vaccine, measles vaccine, mumps vaccine, rubella vaccine, varicella vaccine, *streptococcus pneumoniae* Ty (live mutant bacteria) vaccine, Vi (Vi capsular polysaccharide) vaccine, DT (toxoid) vaccine, Td (toxoid) vaccine, aP (inactive bacterial antigen/accelular (DtaP)) vaccine, Hib (bacterial polysaccharide-protein conjugate) vaccine, hepatitis B virus (inactive serum derived viral antigen/recombinant antigen) vaccine, influenza vaccine, rotavirus vaccine, respiratory syncytial virus (RSV) vaccine, human astrovirus vaccine, rotavirus vaccine, human influenza A and B virus vaccine, hepatitis A virus vaccine, live attenuated parainfluenza virus type 3 vaccine, enterovirus vaccines, retrovirus vaccines, and picornavirus vaccines.

Diseases capable of treatment with the compositions and methods of the present invention include, for example, without limitation, tumors is associated with the liver, kidney, acute lymphoblastic leukemia, acute myeloid leukemia, ewing's sarcoma, gestational trophoblastic carcinoma, hodgkin's disease, non-Hodgkin's lymphoma, burkitt's lymphoma diffuse large cell lymphoma, follicular mixed lymphoma, lymphoblastic lymphoma, rhabdomyosarcoma, testicular carcinoma, wilms's tumor, anal carcinoma, bladder carcinoma, breast carcinoma, chronic lymphocytic leukemia, chronic myelogenous leukemia, hairy cell leukemia, head and neck carcinoma, lung (small cell) carcinoma, multiple myeloma, Non-Hodgkin's lymphoma, follicular lymphoma, ovarian carcinoma, brain tumors (astrocytoma), cervical carcinoma, colorectal carcinoma, hepatocellular carcinoma, kaposi's sarcoma, lung (non-small-cell) carcinoma, melanoma, pancreatic carcinoma, prostate carcinoma, soft tissue sarcoma, breast carcinoma, colorectal carcinoma (stage III), osteogenic sarcoma, ovarian carcinoma (stage III), testicular carcinoma, or combinations thereof.

Enzymes, include, for example, without limitation, alkaline phosphatase, cyclooxygenase type I and agonists and antagonists.

Anti-allergenic agents, include, for example, without limitation, amelexanox.

Anti-coagulation agents, include, for example, without limitation, phenprocoumon and heparin.

Circulatory drugs, include, for example, without limitation, propranolol.

Anti-tubercular agents, include, for example, without limitation, para-aminosalicylic acid, isoniazid, capreomycin sulfate cycloserine, ethambutol hydrochloride ethionamide, pyrazinamide, rifampin, and streptomycin sulfate.

Anti-viral agents, include, for example, without limitation, acyclovir, amantadine azidothymidine (AZT or Zidovudine), ribavirin, and vidarabine monohydrate (adenine arabinoside, ara-A).

Anti-anginal agents, include, for example, without limitation, diltiazem, nifedipine, verapamil, erythritol tetranitrate, isosorbide dinitrate, nitroglycerin (glyceryl trinitrate), and pentaerythritol tetranitrate.

Antibiotics, include, for example, dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin, rifampin, and tetracycline.

Anti-inflammatory agents and analgesics, include, for example, diflunisal, ibuprofen, indomethacin, meclofenamate, mefenamic acid, naproxen, oxyphenbutazone, phenylbutazone, piroxicam, sulindac, tolmetin, aspirin and salicylates.

Anti-protozoan agents, include, for example, without limitation, chloroquine, metronidazole, hydroxychloroquine, quinine, and meglumine antimonate.

Anti-rheumatic agents, include, for example, without limitation, penicillamine.

Narcotics, include, for example, without limitation, paregoric and opiates, such as codeine, heroin, methadone, morphine and opium.

Cardiac glycoside agents, include, for example, without limitation, deslanoside, digitoxin, digoxin, digitalin and digitalis.

Neuromuscular blocking agents, include, for example, without limitation, atracurium mesylate, gallamine triethiodide, hexafluorenium bromide, metocurine iodide, pancuronium bromide, succinylcholine chloride (suxamethonium chloride), tubocurarine chloride, and vecuronium bromide.

Sedatives (hypnotics), include, for example, without limitation, amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride paraldehyde, pentobarbital, pentobarbital sodium, phenobarbital sodium, secobarbital sodium, talbutal, temazepam, and triazolam.

Local anesthetic agents, include, for example, without limitation, bupivacaine hydrochloride, chloroprocaine hydrochloride, etidocaine hydrochloride, lidocaine hydrochloride, mepivacaine hydrochloride, procaine hydrochloride, and tetracaine hydrochloride.

General anesthetic agents, include, for example, without limitation, droperidol, etomidate, fentanyl citrate with droperidol, ketamine hydrochloride, methohexital sodium, and thiopental sodium.

Radioactive particles or radioactive ions, include, for example, without limitation, strontium, rhenium, yttrium, technetium, and cobalt.

Preferably, the bioactive therapeutic factor is an antineoplastic agent, a hormone, a steroid, an anti-fungal agent, a peptide or a peptide analog. More preferably, the bioactive agent is dexamethasone, amphotericin B, adriamycin, mitomycin c, taxol, doxorubicin, or tissue plasminogen activator (t-PA). The bioactive therapeutic factor used in the present invention are preferably highly active in low concentrations. The targeting aspects of the invention further enable lowered dosages to be applied for therapy, since the effective concentration at the therapeutic site remains undiluted in the body. The amount of the bioactive therapeutic factor of the present invention to be administered to a patient depends, for example, on the particular bioactive therapeutic factor that is used, the method in which the bioactive therapeutic factor is being administered, and the age, sex, weight and physical condition of the patient. Generally, treatment is initiated with small dosages, which can then be increased by small increments, until the desired effect under the circumstances is achieved. Additionally, one skilled in the art may rely on reference materials, such as the Physician's Desk Reference, published by Medical Economics Company at Montvale, N.J. 07645-1742, to determine the appropriate amount of a particular bioactive therapeutic factor, and hence the corresponding prodrug of the invention that may be administered to a patient in the case of combination therapeutic drug and gene therapy using the methods of the present invention. In accordance with the present invention, the prodrug is delivered to the patient (e.g., in a region of the patient) for the purposes, for example, of treating a condition (i.e., a disease state, malady, disorder, etc.) in the patient. The prodrugs may be used as above or may be incorporated into other embodiments, such as emulsions.

4.5 Transfection Agents for Polynucleotide Delivery

Genetic material comprising nucleic acids, polynucleotides, RNA and DNA, of either natural or synthetic origin, including recombinant RNA and DNA and antisense RNA and DNA; hammerhead RNA, ribozymes, antigene nucleic acids, both single and double stranded RNA and DNA and analogs thereof, either in combination or not with other elements such as, for example, without limitation, tissue specific enhancers, and nuclear localization signals, can be introduced into eukaryotic cells via conventional transformation or transfection techniques. As used herein, the terms "transformation" and "transfection" are intended to refer to a variety of art-recognized techniques for introducing foreign nucleic acid into a host cell, including, for example, without limitation, calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

In order to obtain an efficient in vivo transfer of the bioactive therapeutic compositions of the present invention, various transfection agents are employed. Representative examples of transfection agents which are suitable for use with the methods of the present invention include, without limitation, calcium phosphate or calcium chloride co-precipitation, DEAE-dextran-mediated transfection, quaternary ammonium amphiphile DOTMA ((dioleoyloxypropyl) trimethylammonium bromide, commercialized as Lipofectin by GIBCO-BRL)) (Feigner et al, (1987) *Proc. Natl. Acad. Sci. USA* 84, 7413-7417; Malone et al. (1989) *Proc. Natl. Acad. Sci. USA* 86 6077-6081); lipophilic glutamate diesters with pendent trimethylammonium heads (Ito et al. (1990) *Biochem. Biophys. Acta* 1023, 124-132); the metabolizable parent lipids such as the cationic lipid dioctadecylamido glycyl-spermine (DOGS, Transfectam, Promega) and dipalmitoylphosphatidyl ethanolamylspermine (DPPES) (J. P. Behr (1986) *Tetrahedron Lett.* 27, 5861-5864; J. P. Behr et al. (1989) *Proc. Natl. Acad. Sci. USA* 86, 6982-6986); metabolizable quaternary ammonium salts (DOTB, N-(1 [2,3-dioleoyloxy]propyl)-N,N,N-trimethylammonium methylsulfate (DOTAP) (Boehringer Mannheim), polyethyleneimine (PEI), dioleoyl esters, ChoTB, ChoSC, DOSC) (Leventis et al. (1990) *Biochim. Inter.* 22, 235-241); 3beta[N—(N',N'-dimethylaminoethane)-carbamoyl]cholesterol (DC-Chol), dioleoylphosphatidyl ethanolamine (DOPE)/3beta [N—(N',N'-dimethylaminoethane)-carbamoyl] cholesterolDC-Chol in one to one mixtures (Gao et al., (1991) *Biochim. Biophys. Acta* 1065, 8-14), spermine, spermidine, lipopolyamines (Behr et al., Bioconjugate Chem, 1994, 5:382-389), lipophilic polylysines (LPLL) (Zhou et al., (1991) *Biochim. Biophys. Acta* 939, 8-18), [[(1,1,3,3-tetramethylbutyl)cresoxy]ethoxy]ethyl]dimethylbe nzylammonium hydroxide (DEBDA hydroxide) with excess phosphatidylcholine/cholesterol (Ballas et al., (1988) *Biochim. Biophys. Acta* 939, 8-18), cetyltrimethylammonium bromide (CTAB)/DOPE mixtures (Pinnaduwage et al., (1989) *Biochim. Biophys. Acta* 985, 33-37), lipophilic diester of glutamic acid (TMAG) with DOPE, CTAB, DEBDA, didodecylammonium bromide (DDAB), and stearylamine in admixture with phosphatidylethanolamine (Rose et al., (1991) *Biotechnique* 10, 520-525), DDAB/DOPE (TransfectACE, GIBCO BRL), and oligogalactose bearing lipids (Remy et al., to be published).

Also encompassed within the present invention is the use of various transfection enhancer agents to increase the efficiency of transfer of the bioactive therapeutic factor into cells. Suitable transfection enhancer agents include, for example, without limitation, DEAE-dextran, polybrene, lysosome-disruptive peptide (Ohmori N I et al., *Biochem Biophys Res Commun* 1997 June 27; 235(3):726-9), chondroitan-based proteoglycans, sulfated proteoglycans, polyethylenimine, polylysine (Pollard H et al. J Biol Chem, 1998 273 (13):7507-11), integrin-binding peptide CYGGRGDTP, linear dextran nonasaccharide, glycerol, cholesteryl groups tethered at the 3'-terminal internucleoside link of an oligonucleotide (Letsinger, R. L. 1989 *Proc Natl Acad Sci USA* 86: (17):6553-6), lysophosphatide, lysophosphatidylcholine, lysophosphatidylethanolamine, and 1-oleoyl lysophosphatidylcholine.

Preferred examples of suitable transfection agents include, without limitation, lipopolyamines as disclosed in U.S. Pat. No. 5,171,678, issued to Behr, et al., Dec. 15, 1992, U.S. Pat. No. 5,476,962 issued to Behr, et al., Dec. 19, 1995, and U.S. Pat. No. 5,616,745 issued to Behr, et al., Apr. 1, 1997, the entire disclosures of which are incorporated herein by reference in their entirety.

Particularly preferred transfection agents of the present invention comprise lipopolyamines of general formula (I) as disclosed in U.S. Pat. No. 5,171,678, issued to Behr, et al., Dec. 15, 1992, U.S. Pat. No. 5,476,962 issued to Behr, et al., Dec. 19, 1995, and U.S. Pat. No. 5,616,745 issued to Behr, et al., Apr. 1, 1997.

The lipopolyamines of general formula (I) are especially useful as vectors for the transfection of eukaryotic cells. The lipopolyamines of general formula (I) have the property, when dispersed in water, of forming unilamellar nanoparticles which are unstable in an ionic medium and which associate strongly, via their cationic portion, with plasmid or oligonucleotide DNA, compacting the latter and covering it with a lipid layer. By using an excess of cationic charges relative to the nucleic acid, the lipid/DNA complexes may be adsorbed on cell membranes, thereby facilitating uptake of the DNA by the cells.

Such lipopolyamines of the general formula (I) additionally enable fragile cells (examples of which include, without limitation, intermediate or anterior hypophyseal cells, chromaffin cells, peripheral or central neurons), which it was not possible to transfect by the application of classical methods (calcium phosphate coprecipitation or dextran techniques), to be transfected.

4.6 Recombinant Expression Vectors

Another aspect of the invention pertains to the delivery of vectors either with or without embolization. Preferably the expression vectors contain a nucleic acid encoding a bioactive therapeutic factor or polypeptide of the invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Specific examples of viral vectors, include, without limitation, adenovirus and retrovirus vectors for gene therapy using the microspheres and transfection agents of the invention. Also contemplated within the present invention is the use of a virus-like particle containing a bioactive therapeutic factor, wherein the virus-like particle is physically linked to the transfection agent, which is also linked to the microparticle. Also contemplated within the present invention is the use of a virus-like particle containing a bioactive therapeutic factor, wherein the virus-like particle is physically linked to the transfection agent, which is also linked to the microparticle.

Such virus-like particles may be designed using polyethylenimine (PEI) conjugated to the integrin-binding peptide CYG-GRGDTP via disulphide bridge formation. Such PEI/RGD-containing peptide complexes share with adenovirus constitutive properties such as size and a centrally protected core, as well as early properties, such as cell entry mediated by integrins and acid-triggered endosome escape (Erbacher et al., to be published).

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic (e.g., *E. coli*) or eukaryotic cells (e.g., insect cells (using baculovirus expression vectors), yeast cells, or mammalian cells). Suitable host cells are discussed further in Goeddel, supra. Alternatively, the recombinant expression vector can be transcribed and translated in vitro, for example using T7 promoter regulatory sequences and T7 polymerase.

In another embodiment, a nucleic acid of the invention is expressed in mammalian cells using a mammalian expression vector. Examples of mammalian expression vectors include pCDM8 (Seed (1987) *Nature* 329:840) and pMT2PC (Kaufinan et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), prostate-specific promoters and/or enhancers (U.S. Pat. Nos. 5,830,686, and 5,871,726, the entire of which are incorporated herein by reference in their entirety) and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a given polypeptide.

Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (*Reviews—Trends in Genetics*, Vol. 1(1) 1986).

In one aspect of the present invention, various cancers may be treated by supplying a toxin gene on a DNA template with a tissue specific enhancer and/or promoter to focus expression of the gene in the cancer cells. For example, toxin genes include, without limitation, the diphtheria toxin gene. Intracellular expression of diphtheria toxin is known to kill cells. The use of certain promoters could be tissue-specific such as using a pancreas-specific promoter for pancreatic cancer. Thus, a functional diphtheria toxin gene delivered to pancreatic cells could, in theory, eradicate the entire pancreas. This strategy could be used as a treatment for pancreatic cancer. The tissue specific enhancer would ensure that expression of diphtheria toxin would only occur in pancreatic cells. DNA/lipopolyamine/microsphere complexes containing the diphtheria toxin gene under the control of a tissue specific enhancer would be introduced directly into a cannulated artery feeding the pancreas. The infusion would occur on some dosing schedule for as long as necessary to eradicate the pancreatic tissue. Other lethal genes besides diphtheria toxin could be used with similar effect, such as genes for ricin or cobra venom factor or enterotoxin.

Another specific example would be the use of prostate specific antigen promoter/enhancer to direct a bioactive therapeutic factor of the present invention to the prostate of a patient in need of treatment for prostatic cancer. One could also treat specialized cancers by the transfer of genes such as, for example, without limitation, the p53 gene, the retinoblastoma gene (and others of that gene family) that suppress the cancer properties of certain cancers.

4.7 Adenovirus-Mediated Gene Transfer

For the purpose of gene therapy, adenoviruses carrying deletions have been proposed as suitable vehicles. Adenoviruses are non-enveloped DNA viruses. Gene-transfer vectors derived from adenoviruses (so-called adenoviral vectors) have a number of features that make them particularly useful for gene transfer for such purposes. For example, the biology of the adenoviruses is characterized in detail, the adenovirus is not associated with severe human pathology, the virus is extremely efficient in introducing its DNA into the host cell, the virus can infect a wide variety of cells and has a broad host-range, the virus can be produced in large quantities with relative ease, and the virus can be rendered replication defective by deletions in, inter alia, the early-region 1 (E1) of the viral genome.

The adenovirus genome is a linear double-stranded DNA molecule of approximately 36,000 base pairs with the 55-kDa terminal protein covalently bound to the 5' terminus of each DNA strand. The Ad DNA contains identical Inverted Terminal Repeats (ITRs) of about 100 base pairs with the exact length depending on the serotype. The viral origins of replication are located within the ITRs exactly at the genome ends. DNA synthesis occurs in two stages. First, the replication proceeds by strand displacement, generating a daughter duplex molecule and a parental displaced strand. The displaced strand is single-stranded and can form a so-called "panhandle" intermediate, which allows replication initiation and generation of a daughter duplex molecule. Alternatively, replication may proceed from both ends of the genome simultaneously, obviating the requirement to form the panhandle structure.

During the productive infection cycle, the viral genes are expressed in two phases: the early phase, which is the period up to viral DNA replication, and the late phase, which coincides with the initiation of viral DNA replication. During the early phase only the early gene products, encoded by regions E1, E2, E3 and E4, are expressed, which carry out a number of functions that prepare the cell for synthesis of viral structural proteins (Berk, 1986). During the late phase the late viral gene products are expressed in addition to the early gene products and host cell DNA and protein synthesis are shut off. Consequently, the cell becomes dedicated to the production of viral DNA and of viral structural proteins (Tooze, 1981).

There are various adenovirus serotypes whose structure and properties vary somewhat. Among these serotypes, the use, within the framework of the present invention, of the type 2 or 5 human adenoviruses (Ad 2 or Ad 5) or the adenoviruses of animal origin (see Application WO94/26914, the disclosure of which is incorporated herein by reference in its entirety) is preferred. Among the adenoviruses of animal origin which can be used within the framework of the present invention, adenoviruses of canine, bovine, murine (example: Mav1, Beard et al., Virology 75 (1990) 81), ovine, porcine, avian or alternatively simian (example: SAV) origin are contemplated. Preferably, the adenovirus of animal origin is a canine adenovirus, more preferably a CAV-2 adenovirus [Manhattan or A26/61 strain (ATCC VR-800), for example]. Preferably, adenoviruses of human or canine or mixed origin may be used for the methods of the invention.

The defective recombinant adenoviruses for use in the methods of the invention can be prepared by any technique known to persons skilled in the art (Levrero et al., Gene 101 (1991) 195, EP 185 573; Graham, EMBO J. 3 (1984) 2917). In particular, they can be prepared by homologous recombination between an adenovirus and a plasmid carrying, inter alia, a cassette containing a gene of interest. The homologous recombination occurs after cotransfection of the adenovirus and plasmid into an appropriate cell line. The cell line used should preferably (i) be transformable by the said elements, and (ii) contain the sequences capable of complementing the defective adenovirus genome part, preferably in integrated form in order to avoid risks of recombination. As an example of a cell line, there may be mentioned the human embryonic kidney line 293 (Graham et al., J. Gen. Virol. 36 (1977) 59) which contains especially, integrated into its genome, the left-hand part of the genome of an Ad5 adenovirus (12%). Strategies for constructing vectors derived from adenoviruses have also been described in applications Nos. WO94/26914 and FR 2,707,664, each of which are herein incorporated by reference in their entirety.

4.8 Retrovirus Particle-Mediated Gene Transfer

Retroviral vectors are gene transfer vehicles for mammals that exploit features of the retrovirus replication cycle such as high infection efficiency and stable co-linear integration of the virally transmitted information in a target cell chromosome. Retroviral vectors are becoming important tools in basic research, biotechnology and gene therapy.

Most retroviral vectors currently in use are derived from Murine Leukemia Viruses (MLVs). MLVs are particularly suitable as vectors due to their well-documented pattern of transcription in diverse cell types and relatively simple modular genetic structure.

Retroviral structure: Retroviruses belong among the enveloped viruses. The bilipid envelope is derived from the host cell membrane and modified by the insertion of the viral surface protein (SU) and transmembrane protein (TM). The matrix protein (MA) is situated just under the outer membrane surrounding the inner core. The core consists of capsid protein (CA). Inside the capsid are two copies of the retroviral genome which are attached to each other at the 5' end via hydrogen bonding. The virus core particle also contains the viral enzymes: reverse transcriptase (RT), protease (PR), and integrase (IN), and the nucleocapsid protein (NC) which is bound to the viral genome. Besides these proteins encoded by the virus, the virion also contains a number of tRNA molecules derived from the host cell tRNA population.

Murine leukemia viruses (MLV) belong to the simple retroviruses. Retroviruses have a characteristic genomic map: Two long terminal repeats (LTRs) flanking the three structural genes gag, pol and env. The LTRs can be subdivided into three regions: The U3 region containing the enhancer and promoter elements recognized by the cellular transcription machinery, the R region which play an important role during reverse transcription and furthermore contains the polyadenylation signal, and the U5 region containing sequences of importance in reverse transcription and packaging of the retroviral genome. Additionally, the LTRs contain cis elements, the inverted repeats, important during the process of integration.

The integrated provirus gives rise to two mRNA transcripts, a full-length mRNA encoding the gag-, and the gag-pol polyproteins, and a spliced mRNA encoding the envelope glycoproteins. The full-length mRNA also serves as the genomic RNA and, besides the already described components of the LTR moieties, contains three important cis elements in the 5' untranslated sequence. The primer binding site (PBS), situated downstream from the U5 region, consists of 18 nucleotides complementary to the 3' end of the primer tRNA molecule. Also located in the 5' untranslated region, between the PBS and the beginning of the gag open reading frame, is the packaging signal (.PSI.). The 5' untranslated region furthermore contains a dimer linkage domain responsible for the dimerization of the two viral genomes in the virion. Immediately upstream from the U3 region is another important cis-element, the polypurine tract (PP), which consists of a stretch of A and G residues. This element serves as a site for priming plus-strand DNA synthesis during reverse transcription.

The retroviral lifecycle: Two different mechanisms have been proposed to explain the entry of the virus particle into the host cytoplasm. Most retroviruses, including MLV, are thought to enter the host cell through receptor-mediated endocytosis, a process in which the whole enveloped virus particle is internalized into an endosomal body. The receptor molecule for the ecotropic murine leukemia viruses has been cloned and identified as a cationic amino acid transporter.

After the viral core particle has entered the cytoplasm of the host cell, all enzymatic functions leading to the integrated double-stranded DNA provirus are managed by viral proteins synthesized in the previous host cell and brought along in the virion. The fate of the viral proteins after entry of the core particle is not clear, but the reverse transcriptase, the integrase and the capsid protein remain with the RNA genome forming the nucleoprotein complex in which reverse transcription occurs. Recently, also the matrix protein has been found in association with the nucleoprotein complex.

Following reverse transcription, the nucleoprotein complex migrates to the host cell nucleus. The mechanism responsible for the nuclear localization is unclear, although evidence from Rous sarcoma virus (RSV) suggests the IN protein to be important since the RSV IN protein, when produced in mammalian cells, is localized in the nucleus. Entry of the nucleoprotein complex into the nucleus requires mitosis, probably because the nucleoprotein complex cannot penetrate the nuclear envelope. Once in the nucleus, integration is mediated by the IN protein. The IN protein recognizes the conserved inverted repeats at the ends of the LTRs and removes 2 bases from the 3' hydroxyl termini of both strands. The IN protein also catalyzes a cleavage in the host DNA and mediates the connections between the proviral DNA and the host DNA. As for the specificity of integration no consensus host DNA target sequence has been found, although a tendency to integrate near DNase I-hypersensitive sites has been reported.

For the simple retroviruses (including MLV) transcription and translation is performed by the host cell machinery. Complex viruses (including HIV and HTLV) encode transactivating proteins involved in transcriptional regulation. The assembly of MLV particles takes place at the host membrane, and the process coincides with the budding process. In mammalian B and C type viruses (MMTV and HTLV, respectively) viral core particles are assembled in the host cell cytoplasm. Encapsidation of the viral genomic RNA is mediated through binding of the cis-acting encapsidation signal and the NC moiety of the Gag- or the Gag-Pol precursor protein.

After budding, the Gag- and Gag-Pol polyproteins are cleaved by viral protease (PR). Maturation of the viral proteins results in an overall change in virion morphology. In addition to proteolytic cleavage of the viral polyproteins following budding of the virus particle, the genomic RNA also undergoes a maturation process resulting in a compact dimeric genome.

Retrovirus Vectors: Retroviruses from which retroviral plasmid vectors may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., Biotechniques, Vol. 7, No. 9,980-990 (1989), or any other promoter (e.g., cellular promoters such as eukaryotic cellular promoters including, but not limited to, the histone, pol III, and 6-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the bioactive therapeutic factor of interest is placed under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the bioactive therapeutic factor of interest.

The retroviral plasmid vector is employed to transduce packaging cell lines to form producer cell lines. Examples of packaging cells which may be transfected include, but are not limited to, the PE501, PA317.psi.-2, .psi.-AM, PA12, T19-14X, VT-19-17-H2, .psi.CRE, psi.CRIP, GP+E-86, GP+envAm12, and DNA cell lines as described in Miller, Human Gene Therapy, Vol. 1, pgs. 5-14 (1990), which is incorporated herein by reference in its entirety. The vector may transduce the packaging cells through any means known in the art. Such means include, but are not limited to, electroporation, the use of liposomes, and $CaPO_4$ precipitation.

The producer cell line generates infectious retroviral vector particles which include the polynucleotide sequence(s) encoding the bioactive therapeutic factor of interest. Such retroviral vector particles then may be employed, to transduce eukaryotic cells, either in vitro or in vivo. The transduced eukaryotic cells will express the polynucleotide sequence(s) encoding the bioactive therapeutic factor of interest. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

In one embodiment, the retroviral plasmid vector which include the polynucleotide sequence(s) encoding the bioactive therapeutic factor of interest may be coupled to a lipid as described supra, and then administered to a host. In one preferred embodiment, the retroviral plasmid vector may be associated with a lipopolyamine transfection agent of the present invention to form a complex which is then mixed with the microspheres of the present invention prior to administration to a patient in need of embolization gene therapy.

4.9 Antisense Gene Therapy

The present invention additionally encompasses the delivery of antisense nucleic acid molecules either with or without embolization. Antisense nucleic acid molecules are those molecules which are complementary to a sense nucleic acid encoding a polypeptide of the invention, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, β-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylamino methyluracil, 5-methoxyaminomethyl-2-thiouracil, β-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl 2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a selected polypeptide of the invention to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection of the antisense nucleic acid molecule/lipopolyamine transfection agent complex/microsphere at a particular tissue site.

Alternatively, antisense nucleic acid molecules can be modified for delivery to target selected cells and then administered systemically using the microspheres and transfection agents of the present invention. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. Such peptides or antibodies can serve to augment the enhanced delivery which is obtained with the microspheres and transfection agents of the present invention. The antisense nucleic acid molecules can also be delivered to cells using the vectors described supra. To achieve sufficient intracellular concentrations of the antisense molecules, vector constructs in which the antisense nucleic acid molecule is placed under the control of a strong pol II or pol III promoter are preferred. An antisense nucleic acid molecule of the invention can be an α-anomeric nucleic acid molecule.

An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

The present invention additionally encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave mRNA transcripts to thereby inhibit translation of the protein encoded by the mRNA. A ribozyme having specificity for a nucleic acid molecule encoding a polypeptide of the invention can be designed based upon the nucleotide sequence of a target gene of interest. For example, a derivative of a *Tetrahymena* L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a bioactive therapeutic factor of the invention can be used to select a catalytic RNA having a specific ribonuclease activity from a pool of RNA molecules. See, e.g., Bartel and Szostak (1993) *Science* 261: 1411-1418.

The invention also encompasses nucleic acid molecules which form triple helical structures. For example, expression of a bioactive therapeutic factor of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4(1):5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications of the present invention. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996) *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or most preferably, by the use of lipopolyamines as transfection agents for complexing with the PNAs prior to association with the microspheres of the present invention. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxythymidine phosphoramidite can be used as a link between the PNA and the 5' end of DNA (Mag et al. (1989) *Nucleic Acids Res.* 17:5973-88). PNA monomers are then coupled in a stepwise manner to produce a chimeric molecule with a 5' PNA segment and a 3' DNA segment (Finn et al. (1996) *Nucleic Acids Res.* 24(17):3357-63). Alternatively, chimeric molecules can be synthesized with a 5' DNA segment and a 3' PNA segment (Peterser et al. (1975) *Bioorganic Med. Chem. Lett.* 5:1119-11124).

In other embodiments, the oligonucleotide may include other appended groups such as peptides (e.g., for targeting host cell receptors in vivo), or agents facilitating transport across cell membranes (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958-976) or intercalating agents (see, e.g., Zon (1988) *Pharm. Res.* 5:539-549). To this end, the oligonucleotide may be conjugated to another molecule, e.g., a peptide, hybridization triggered cross-linking agent, transport agent, hybridization-triggered cleavage agent, etc., prior to or alternatively after, association with the lipolyamine transfection agent and microspheres of the present invention.

4.10 Active Embolization for Drug Delivery and Gene Therapy

One aspect of the present invention is the administration of drugs, vaccines, and diagnostic or imaging agents to a mammal using microspheres. Of course, this embodiment does not necessarily require the use of a transfection agent. However, such an agent is optional due to its ability to associate with the microsphere and the bioactive agent, i.e., act as a linker or its ability to improve endocytosis.

Within one aspect of the present invention methods are provided for embolizing a blood vessel, comprising the step of delivering into the vessel a therapeutically effective amount of a bioactive therapeutic factor transfection agent microsphere composition, such that the blood vessel is effectively occluded. Therapeutically effective amounts suitable for occluding blood vessels may be readily determined given the disclosure provided above. Within a particularly preferred embodiment, the bioactive therapeutic factor transfection agent microsphere composition is delivered to a blood vessel which nourishes a tumor.

Briefly, there are a number of clinical situations (e.g., bleeding, tumor development) where it is desirable to reduce or abolish the blood supply to an organ or region. As described in greater detail below, this may be accomplished by injecting the bioactive therapeutic factor transfection agent microsphere compositions of the present invention into a desired blood vessel through a selectively positioned needle or catheter. The composition travels via the blood stream until it becomes wedged in the vasculature, thereby physically (or chemically) occluding the blood vessel. The reduced or abolished blood flow to the selected area results in infarction (cell death due to an inadequate supply of oxygen and nutrients) or reduced blood loss from a damaged vessel.

For use in embolization therapy, bioactive therapeutic factor transfection agent microsphere compositions of the present invention are preferably non-toxic, thrombogenic, easy to inject down vascular catheters, radio-opaque, rapid and permanent in effect, sterile, and readily available in different shapes or sizes at the time of the procedure. In addition, the compositions preferably result in the slow (ideally, over a period of several weeks to months) release of bioactive therapeutic factor. Particularly preferred bioactive therapeutic factor compositions should have a predictable size of 15-200 µm after being injected into the vascular system. Preferably, they should not clump into larger particles either in solution or once injected. In addition, preferable compositions should not change physical properties during storage prior to use.

Embolization therapy of the present invention may be utilized in at least three principal ways to assist in the management of neoplasms: (1) definitive treatment of tumors (usually benign); (2) for preoperative embolization; and (3) for palliative embolization. Briefly, benign tumors may sometimes be successfully treated by embolization therapy alone. Examples of such tumors include simple tumors of vascular origin (e.g., haemangiomas), endocrine tumors such as parathyroid adenomas, and benign bone tumors.

For other tumors, (e.g., renal adenocarcinoma), preoperative embolization may be employed hours or days before surgical resection in order to reduce operative blood loss, shorten the duration of the operation, and reduce the risk of dissemination of viable malignant cells by surgical manipulation of the tumor. Many tumors may be successfully embolized preoperatively, including for example nasopharyngeal tumors, glomus jugular tumors, meningiomas, chemodectomas, and vagal neuromas.

Embolization may also be utilized as a primary mode of treatment for inoperable malignancies, in order to extend the survival time of patients with advanced disease. Embolization may produce a marked improvement in the quality of life of patients with malignant tumors by alleviating unpleasant symptoms such as bleeding, venous obstruction and tracheal compression. The greatest benefit from palliative tumor embolization, however, may be seen in patients suffering from the humoral effects of malignant endocrine tumors, wherein metastases from carcinoid tumors and other endocrine neoplasms such as insulinomas and glucagonomas may be slow growing, and yet still cause great distress by virtue of the endocrine syndromes which they produce.

In general, embolization therapy utilizing the bioactive therapeutic factor transfection agent microsphere compositions of the present invention is typically performed in a similar manner, regardless of the site. Briefly, angiography of the area to be embolized is first performed by injecting a radiopaque contrast agent through a catheter inserted into an artery or vein as an X-ray is taken. The catheter may be inserted either percutaneously or by surgery. The blood vessel is then embolized by refluxing a bioactive therapeutic factor transfection agent microsphere composition of the present invention through the catheter, until flow is observed to cease. Occlusion may be confirmed by repeating the angiogram.

Embolization therapy generally results in the distribution of compositions containing bioactive therapeutic factors throughout the interstices of the tumor or vascular mass to be treated. The physical bulk of the embolic particles clogging the arterial lumen results in the occlusion of the blood supply. In addition to this effect, the presence of a bioactive therapeutic factor(s) prevents the formation of new blood vessels to supply the tumor or vascular mass, enhancing the devitalizing effect of cutting off the blood supply.

Therefore, it should be evident that a wide variety of tumors may be embolized utilizing a bioactive therapeutic factor transfection agent microsphere composition of the present invention. Briefly, tumors are typically divided into two classes: benign and malignant. In a benign tumor the cells retain their differentiated features and do not divide in a completely uncontrolled manner. In addition, the tumor is localized and non-metastatic. In a malignant tumor, the cells become undifferentiated, do not respond to the body's growth and hormonal signals, and multiply in an uncontrolled manner; the tumor is invasive and capable of spreading to distant sites (metastasizing).

Within one aspect of the present invention, metastases (secondary tumors) of the liver may be treated utilizing embolization therapy. Briefly, a catheter is inserted via the femoral or brachial artery and advanced into the hepatic artery by steering it through the arterial system under fluoroscopic guidance. The catheter is advanced into the hepatic arterial tree as far as necessary to allow complete blockage of the blood vessels supplying the tumor(s), while sparing as many of the arterial branches supplying normal structures as possible. Ideally this will be a segmental branch of the hepatic artery, but it could be that the entire hepatic artery distal to the origin of the gastroduodenal artery, or even multiple separate arteries, will need to be blocked depending on the extent of tumor and its individual blood supply. Once the desired catheter position is achieved, the artery is embolized by injecting anti-angiogenic therapeutic compositions through the arterial catheter until flow in the artery to be blocked ceases, preferably even after observation for 5 minutes. Occlusion of the artery may be confirmed by injecting radiopaque contrast through the catheter and demonstrating by fluoroscopy or X-ray film that the vessel which previously filled with contrast no longer does so. The same procedure may be repeated with each feeding artery to be occluded.

Within another aspect of the present invention, active therapeutic embolization therapy may be used during surgery to remove a tumor or vascular mass or cancerous organ. Additionally, another aspect of the present invention concerns the use of active therapeutic embolization therapy to prevent or ameliorate metastasis.

As noted above, both benign and malignant tumors may be embolized utilizing anti-angiogenic therapeutic compositions of the present invention. Representative examples of benign hepatic tumors include hepatocellular adenoma, cavernous haemangioma, and focal nodular hyperplasia. Other benign tumors, which are more rare and often do not have clinical manifestations, may also be treated. These include bile duct adenomas, bile duct cystadenomas, fibromas, lipomas, leiomyomas, mesotheliomas, teratomas, myxomas, and nodular regenerative hyperplasia.

Malignant hepatic tumors are generally subdivided into two categories: primary and secondary. Primary tumors arise directly from the tissue in which they are found. Thus, a primary liver tumor is derived originally from the cells which make up the liver tissue (such as hepatocytes and biliary cells). Representative examples of primary hepatic malignancies which may be treated by arterial embolization include hepatocellularcarcinoma, cholangiocarcinoma, angiosarcoma, cystadenocarcinoma, squamous cell carcinoma, and hepatoblastoma.

A secondary tumor, or metastasis, is a tumor which originated elsewhere in the body but has subsequently spread to a distant organ. The common routes for metastasis are direct growth into adjacent structures, spread through the vascular or lymphatic systems, and tracking along tissue planes and body spaces (peritoneal fluid, cerebrospinal fluid, etc.). Secondary hepatic tumors are one of the most common causes of death in the cancer patient and are by far and away the most common form of liver tumor. Although virtually any malignancy can metastasize to the liver, tumors which are most likely to spread to the liver include: cancer of the stomach, colon, and pancreas; melanoma; tumors of the lung, oropharynx, and bladder; Hodgkin's and non-Hodgkin's lymphoma; tumors of the breast, ovary, and prostate. Each one of the above-named primary tumors has numerous different tumor types which may be treated by arterial embolization (for example, without limitation, there are reportedly over 32 different types of ovarian cancer).

As noted above, embolization therapy utilizing bioactive therapeutic factor transfection agent microsphere compositions of the present invention may also be applied to a variety of other clinical situations where it is desired to occlude blood vessels. Within one aspect of the present invention, arteriovenous malformation may be treated by administration of one of the above-described bioactive therapeutic factor transfection agent microsphere compositions. Briefly, arteriovenous malformations (vascular malformations) refers to a group of diseases wherein at least one (and most typically, many)

abnormal communications between arteries and veins occur, resulting in a local tumor-like mass composed predominantly of blood vessels. Such disease may be either congenital or acquired.

Within one embodiment of the invention, an arteriovenous malformation may be treated by inserting a catheter via the femoral or brachial artery, and advancing it into the feeding artery under fluoroscopic guidance. The catheter is preferably advanced as far as necessary to allow complete blockage of the blood vessels supplying the vascular malformation, while sparing as many of the arterial branches supplying normal structures as possible (ideally this will be a single artery, but most often multiple separate arteries may need to be occluded, depending on the extent of the vascular malformation and its individual blood supply). Once the desired catheter position is achieved, each artery may be embolized utilizing the bioactive therapeutic factor transfection agent microsphere compositions of the present invention.

Within another aspect of the invention, embolization may be accomplished in order to treat conditions of excessive bleeding. For example, menorrhagia (excessive bleeding with menstruation) may be readily treated by embolization of uterine arteries. Briefly, the uterine arteries are branches of the internal iliac arteries bilaterally. Within one embodiment of the invention, a catheter may be inserted via the femoral or brachial artery, and advanced into each uterine artery by steering it through the arterial system under fluoroscopic guidance. The catheter should be advanced as far as necessary to allow complete blockage of the blood vessels to the uterus, while sparing as many arterial branches that arise from the uterine artery and supply normal structures as possible. Ideally a single uterine artery on each side may be embolized, but occasionally multiple separate arteries may need to be blocked depending on the individual blood supply. Once the desired catheter position is achieved, each artery may be embolized by administration of the bioactive therapeutic factor transfection agent microsphere compositions as described above.

In a like manner, arterial embolization may be accomplished in a variety of other conditions, including for example, without limitation, for acute bleeding, vascular abnormalities, central nervous system disorders, and hypersplenism.

4.10.1 Active Embolization with Genetic Therapy

As noted above, embolization therapy utilizing the bioactive therapeutic factor transfection agent microsphere compositions of the present invention may also be applied to a variety of other clinical situations where it is desired to simultaneously occlude blood vessels and administer gene therapy to a patient in need thereof.

Within one preferred aspect of the present invention, compositions are provided comprising (a) a bioactive therapeutic factor, (b) a polymeric carrier, and (c) a transfection agent.

Within another preferred aspect of the present invention, compositions are provided comprising (a) a polynucleotide encoding a bioactive therapeutic factor, (b) a polymeric carrier, and (c) a transfection agent.

Within a most preferred aspect of the invention, compositions are provided comprising (a) a polynucleotide encoding a bioactive therapeutic factor, (b) a cationic cross-linked microsphere, and (c) a lipopolyamine transfection agent.

In this most preferred aspect of the invention, compositions are provided comprising (a) a polynucleotide encoding a bioactive therapeutic factor, (b) a cationic cross-linked microsphere, and (c) a lipopolyamine transfection agent, wherein the polynucleotide comprises RNA and DNA, of either natural or synthetic origin, including recombinant RNA and DNA and antisense RNA and DNA; hammerhead RNA, ribozymes, antigen nucleic acids, both single and double stranded RNA and DNA and analogs thereof; wherein the bioactive therapeutic factor comprises antineoplastic agents, hormones and steroids, vitamins, peptides and peptide analogs, antibodies or fragments thereof, vaccines, enzymes, anti-allergenic agents, circulatory drugs, anti-tubercular agents, anti-viral agents, anti-anginal agents, anti-protozoan agents, anti-rheumatic agents, narcotics, cardiac glycoside agents, sedatives, local anesthetic agents, and general anesthetic agents; wherein the cationic cross-linked microspheres are based on non-toxic, biocompatible, either swellable or non-swellable, substantially spherical, hydrophilic, inert, ionic cross-linked polymers of a size sufficient to embolize and release the bioactive therapeutic factor and wherein the cationic cross-linked microspheres are preferably polymers are selected from the group consisting of sodium acrylate polymer, acrylamide and acrylamide derivative polymers, sodium acrylate and vinyl alcohol copolymer, saponification products of copolymer of vinyl acetate and acrylic acid ester, vinyl acetate and acrylic acid ester copolymer, vinyl acetate and methyl maleate copolymer, isobutylene-maleic anhydride crosslinked copolymer, starch-acrylonitrile graft copolymer and its saponification products, crosslinked sodium polyacrylate polymer, and crosslinked polyethylene oxide; and wherein the preferred examples of suitable transfection agents include, without limitation, lipopolyamines, and polyethlenimine (PEI). Particularly preferred transfection agents of the present invention comprise lipopolyamines of general formula (I) as disclosed in U.S. Pat. No. 5,171,678, issued to Behr, et al., Dec. 15, 1992, U.S. Pat. No. 5,476,962 issued to Behr, et al., Dec. 19, 1995, and U.S. Pat. No. 5,616,745 issued to Behr, et al., Apr. 1, 1997, the entire contents of each of which are incorporated herein by reference.

Within the preferred and most preferred embodiments disclosed herein of the present invention, the bioactive therapeutic factor is physically associated with the transfection agent to form a complex and the bioactive therapeutic factor-transfection agent complex is then physically associated with the polymeric carrier. The bioactive therapeutic factor is preferably adsorbed by means of association forces that are well known in liquid adsorption chromatography including such association forces as, without limitation, ion exchange, hydrophobicity, molecular recognition or combinations thereof. The selected bioactive therapeutic factor is mixed with the transfecting agent and the transfecting agent imparts specific properties to the bioactive therapeutic factor-transfecting agent, such as increased hydrophobicity. The microsphere comprising the embolization material (e.g., Embosphere®) is mixed together with a sufficient amount of a transfectable bioactive therapeutic factor, with the physical association between the transfectable bioactive therapeutic factor and the embolic material being the result of ionic and hydrophobic associations that can be further enhanced by the addition of salts such as, for example, without limitation, sodium chloride.

Within the preferred and most preferred embodiments disclosed herein of the present invention, the bioactive therapeutic factor-transfection agent complexes which are adsorbed on, or associated with, the surface of the embolic material are progressively desorbed and delivered into the surrounding cells by a variety of mechanisms including, for example, without limitation, spontaneous endocytosis, receptor-mediated endocytosis, endosomolysis, and cell membrane destabilization or combinations thereof. The desorption of the bioactive therapeutic factor is induced by natural components of biological liquids that serve to weaken the adsorption strength between the embolic material and the bioactive therapeutic factor until the total desorption of the latter is achieved.

Within another aspect of the present invention, methods are provided for embolizing blood vessels in tumorigenic, angiogenesis-dependent diseases, comprising delivering to the vessel of a patient in need thereof a therapeutically effective amount of a composition comprising a polynucleotide encoding a bioactive factor associated with a transfection agent wherein said polynucleotide encoding a bioactive factor associated with a transfection agent is further associated with a microsphere, such that the blood vessel is effectively occluded, and the tumorigenic, angiogenesis-dependent disease is ameliorated.

4.11 Diagnostic Imaging

As discussed above, the bioactive therapeutic factor transfection agent microspheres composition of the present invention may be used in connection with diagnostic imaging, therapeutic imaging and therapeutic drug delivery, including, for example, ultrasound (US), magnetic resonance imaging (MRI), nuclear magnetic resonance (NMR), computed tomography (CT), electron spin resonance (ESR), nuclear medical imaging, optical imaging, elastography, drug delivery with ultrasound, radiofrequency (RF) and microwave laser. The delivery vehicles and stabilizing materials of the present invention may be used in combination with various contrast agents, including conventional contrast agents, which may serve to increase their effectiveness as contrast agents for diagnostic and therapeutic imaging.

Examples of suitable contrast agents for use in combination with the present stabilizing materials include, for example, stable free radicals, such as, stable nitroxides, as well as compounds comprising transition, lanthanide and actinide elements, which may, if desired, be in the form of a salt or may be covalently or non-covalently bound to complexing agents, including lipophilic derivatives thereof, or to proteinaceous macromolecules. Preferable transition, lanthanide and actinide elements include, for example, Gd(III), Mn(II), Cu(II), Cr(III), Fe(II), Fe(III), Co(II), Er(II), Ni(II), EU(III) and Dy(III). More preferably, the elements may be Gd(III), Mn(II), Cu(II), Fe(II), Fe(III), Eu(III) and Dy(III), most preferably Mn(II) and Gd(III). The foregoing elements may be in the form of a salt, including inorganic salts, such as a manganese salt, for example, manganese chloride, manganese carbonate, manganese acetate, and organic salts, such as manganese gluconate and manganese hydroxylapatite. Other exemplary salts include salts of iron, such as iron sulfides, and ferric salts, such as ferric chloride.

The above elements may also be bound, for example, through covalent or noncovalent association, to complexing agents, including lipophilic derivatives thereof, or to proteinaceous macromolecules. Preferable complexing agents include, for example, diethylenetriaminepentaacetic acid (DTPA), ethylenediaminetetraacetic acid (EDTA), 1,4,7,10-tetraazacyclododecane-N,N',N',N'''-tetraacetic acid (DOTA), 1,4,7,10-tetraazacyclododecane-N,N',N'''-triacetic acid (DOTA), 3,6,9-triaza-12-oxa-3,6,9-tricarboxymethylene-10-carboxy-13-phenyltridecan oic acid (B-19036), hydroxybenzylethylenediamine diacetic acid (HBED), N,N'-bis(pyridoxyl-5-phosphate)ethylene diamine, N,N'-diacetate (DPDP), 1,4,7-triazacyclononane-N,N',N''-triacetic acid (NOTA), 1,4,8,11-tetraazacyclotetradecane-N,N',N'',N'''-tetraacetic acid (TETA), kryptands (macrocyclic complexes), and desferrioxamine. More preferably, the complexing agents are EDTA, DTPA, DOTA, DO3A and kryptands, most preferably DTPA. Preferable lipophilic complexes include alkylated derivatives of the complexing agents EDTA, DOTA, for example, N,N'-bis-(carboxydecylamidomethyl-N-2,3-dihydroxypropyl)ethylenediarnine-N,N'-diacetate (EDTA-DDP); N,N'-bis(carboxyoctadecylamidomethyl-N-2,3-dihydroxypropyl)ethylenediamine-N,N'-diacetate (EDTA-ODP); and N,N'-Bis(carboxy-laurylamidomethyl-N-2,3-dihydroxypropyethylenediamine-N,N'-diacetate (EDTA-LDP); including those described in U.S. Pat. No. 5,312,617, the disclosure of which is hereby incorporated herein by reference in its entirety. Preferable proteinaceous macromolecules include, for example, albumin, collagen, polyarginine, polylysine, polyhistidine, γ-globulin and β-globulin, with albumin, polyarginine, polylysine, and polyhistidine being more preferred. Suitable complexes therefore include Mn(II)-DTPA, Mn(II)-EDTA, Mn(II)-DOTA, Mn(II)-DOT3A, Mn(II)-kryptands, Gd(III)-DTPA, Gd(III)-DOTA, Gd(III)-DO3A, Gd(III)-kryptands, Cr(III)-EDTA, Cu(II)-EDTA, or iron-desferrioxamine, more preferably Mn(II)-DTPA or Gd(III)-DTPA.

Nitroxides are paramagnetic contrast agents which increase both T1 and T2 relaxation rates on MRI by virtue of the presence of an unpaired electron in the nitroxide molecule. As known to one of ordinary skill in the art, the paramagnetic effectiveness of a given compound as an MRI contrast agent may be related, at least in part, to the number of unpaired electrons in the paramagnetic nucleus or molecule, and specifically, to the square of the number of unpaired electrons. For example, gadolinium has seven unpaired electrons whereas a nitroxide molecule has one unpaired electron. Thus, gadolinium is generally a much stronger MRI contrast agent than a nitroxide. However, effective correlation time, another important parameter for assessing the effectiveness of contrast agents, confers potential increased relaxivity to the nitroxides. When the tumbling rate is slowed, for example, by attaching the paramagnetic contrast to a large molecule, it will tumble more slowly and thereby more effectively transfer energy to hasten relaxation of the water protons. In gadolinium, however, the electron spin relaxation time is rapid and will limit the extent to which slow rotational correlation times can increase relaxivity. For nitroxides, however, the electron spin correlation times are more favorable and tremendous increases in relaxivity may be attained by slowing the rotational correlation time of these molecules. Although not intending to be bound by any particular theory of operation, it is contemplated that since the nitroxides may be designed to coat the perimeters of the microspheres, for example, by making alkyl derivatives thereof, the resulting correlation times can be optimized. Moreover, the resulting contrast medium of the present invention may be viewed as a magnetic sphere, a geometric configuration which maximizes relaxivity.

Exemplary superparamagnetic contrast agents suitable for use in the compositions of the present invention include metal oxides and sulfides which experience a magnetic domain, ferro- or ferrimagnetic compounds, such as pure iron, magnetic iron oxide, such as magnetite, $\gamma$-$Fe_2O_3$, $Fe_3O_4$, manganese ferrite, cobalt ferrite and nickel ferrite. MR whole body imaging may then be employed to rapidly screen the body, for example, for thrombosis, and ultrasound may be applied, if desired, to aid in thrombolysis.

The contrast agents, such as the paramagnetic and superparamagnetic contrast agents described above, may be employed as a component within the microspheres and/or stabilizing materials. With respect to vesicles, the contrast agents may be entrapped within the internal void thereof, administered as a solution with the microspheres, incorporated with any additional stabilizing materials, or coated onto the surface or membrane of the vesicle. Mixtures of any one or more of the paramagnetic agents and/or superparamagnetic agents in the present compositions may be used. The paramagnetic and superparamagnetic agents may also be coadministered separately, if desired.

If desired, the paramagnetic or superparamagnetic agents may be delivered as alkylated or other derivatives incorporated into the compositions, especially the lipidic walls of the microspheres. In particular, the nitroxides 2,2,5,5-tetramethyl-1-pyrrolidinyloxy, free radical and 2,2,6,6-tetramethyl-1-piperidinyloxy, free radical, can form adducts with long chain fatty acids at the positions of the ring which are not occupied by the methyl groups via a variety of linkages, including, for example, an acetyloxy linkage. Such adducts are very amenable to incorporation into the bioactive therapeutic factor transfection agent microsphere compositions of the present invention.

The stabilizing materials and/or microspheres of the present invention, and especially the microspheres, may serve not only as effective carriers of the superparamagnetic agents described above, but also may improve the effect of the susceptibility contrast agents. Superparamagnetic contrast agents include metal oxides, particularly iron oxides but including manganese oxides, and as iron oxides, containing varying amounts of manganese, cobalt and nickel which experience a magnetic domain. These agents are nano or microspheres and have very high bulk susceptibilities and transverse relaxation rates. The larger particles, for example, particles having diameters of about 100 nm, have much higher $R_2$ relaxivities as compared to $R_1$ relaxivities. The smaller particles, for example, particles having diameters of about 10 to about 15 nm, have somewhat lower $R_2$ relaxivities, but much more balanced $R_1$ and $R_2$ values. Much smaller particles, for example, monocrystalline iron oxide particles having diameters of about 3 to about 5 nm, have lower $R_2$ relaxivities, but probably the most balanced $R_1$ and $R_2$ relaxation rates. Ferritin can also be formulated to encapsulate a core of very high relaxation rate superparamagnetic iron.

The iron oxides may simply be incorporated into the stabilizing materials and/or microspheres. Preferably, in the case of microspheres formulated from lipids, the iron oxides may be incorporated into the walls of the microspheres, for example, by being adsorbed onto the surfaces of the microspheres, or entrapped within the interior of the microspheres.

4.12 Pharmaceutical Formulations

Therapeutic Formulations: Polynucleotide salts: Administration of pharmaceutically acceptable salts of the polynucleotides encoding bioactive therapeutic factors described herein is included within the scope of the invention. Such salts may be prepared from pharmaceutically acceptable non-toxic bases including organic bases and inorganic bases. Salts derived from inorganic bases include sodium, potassium, lithium, ammonium, calcium, magnesium, and the like. Salts derived from pharmaceutically acceptable organic nontoxic bases include salts of primary, secondary, and tertiary amines, basic amino acids, and the like. For a helpful discussion of pharmaceutical salts, see S. M. Berge et al., Journal of Pharmaceutical Sciences 66:1-19 (1977), the disclosure of which is hereby incorporated by reference.

Polynucleotides encoding bioactive therapeutic factors, admixed or associated with a suitable transfection agent of the present invention conjugated to a microparticle suitable for injection may be prepared in unit dosage form in ampules, or in multidose containers. The polynucleotides may be present in such forms as suspensions, solutions, or emulsions in oily or preferably aqueous vehicles. Alternatively, the polynucleotide salt may be in lyophilized form for reconstitution, at the time of delivery, with a suitable vehicle, such as sterile pyrogen-free water. Both liquid as well as lyophilized forms that are to be reconstituted will comprise agents, preferably buffers, in amounts necessary to suitably adjust the pH of the injected solution. For any parenteral use, particularly if the formulation is to be administered intravenously, the total concentration of solutes should be controlled to make the preparation isotonic, hypotonic, or weakly hypertonic. Non-ionic materials, such as sugars, are preferred for adjusting tonicity, and sucrose is particularly preferred. Any of these forms may further comprise suitable formulatory agents, such as starch or sugar, glycerol or saline. The compositions per unit dosage, whether liquid or solid, may contain from 0.1% to 99% of polynucleotide material.

The units dosage ampules or multidose containers, in which the polynucleotides encoding bioactive therapeutic factors, admixed or associated with a suitable transfection agent of the present invention conjugated to a microparticle are packaged prior to use, may comprise a hermetically sealed container enclosing an amount of polynucleotides encoding bioactive therapeutic factors, admixed or associated with a suitable transfection agent of the present invention conjugated to a microparticle or solution containing a polynucleotides encoding bioactive therapeutic factors, admixed or associated with a suitable transfection agent of the present invention conjugated to a microparticle suitable for a pharmaceutically effective dose thereof, or multiples of an effective dose. The polynucleotides encoding bioactive therapeutic factors, admixed or associated with a suitable transfection agent of the present invention conjugated to a microparticle is packaged as a sterile formulation, and the hermetically sealed container is designed to preserve sterility of the formulation until use.

The container in which the polynucleotides encoding bioactive therapeutic factors, admixed or associated with a suitable transfection agent of the present invention conjugated to a microparticle is packaged is labeled, and the label bears a notice in the form prescribed by a governmental agency, for example the Food and Drug Administration, which notice is reflective of approval by the agency under Federal law, of the manufacture, use, or sale of the polynucleotides encoding bioactive therapeutic factors, admixed or associated with a suitable transfection agent of the present invention conjugated to a microparticle therein for human administration. Federal law requires that the use of pharmaceutical agents in the therapy of humans be approved by an agency of the Federal government. Responsibility for enforcement is the responsibility of the Food and Drug Administration, which issues appropriate regulations for securing such approval, detailed in 21 U.S.C. 301-392. Regulation for biologic material, comprising products made from the tissues of animals is provided under 42 U.S.C. §262. Similar approval is required by most foreign countries. Regulations vary from country to country, but the individual procedures are well known to those in the art.

Dosage and Route of Administration: The dosage to be administered depends to a large extent on the condition and size of the subject being treated as well as the frequency of treatment and the route of administration. Regimens for continuing therapy, including dose and frequency may be guided by the initial response and clinical judgment. The parenteral route of injection into the interstitial space of tissues is preferred, although other parenteral routes, such as inhalation of an aerosol formulation, may be required in specific administration, as for example to the mucous membranes of the nose, throat, bronchial tissues or lungs. In preferred protocols, a formulation comprising the polynucleotide encoding a bioactive therapeutic factor, admixed or associated with a suitable transfection agent of the present invention conjugated to a microparticle in an aqueous carrier is injected into tissue in amounts of from 10 µl per site to about 1 ml per site. The concentration of polynucleotide encoding a bioactive therapeutic factor in the formulation is from about 0.1 µg/ml to about 20 mg/ml.

Preferred formulations for transfection of polynucleotides and peptides into cells comprise cationic lipopolyamine transfection agents of the invention, either with or without an effective transfection-promoting amount of a lysophosphatide. The lysophosphatide may have a neutral or a negative headgroup. Lysophosphatidylcholine and lysophosphatidylethanolamine are preferred, and 1-oleoyl lysophosphatidylcholine is particularly preferred. Lysophosphatide lipids are advantageously present in the formulation in a molar ratio of 0.5 lysolipid to cationic lipid. Lyso forms of cationic lipids, selected from the novel cationic lipids of the invention, DOTMA, or DOTAP can also be used to increase the effectiveness of the transfection. These lyso forms are advantageously present in effective amounts up to about one-third of the total cationic lipid in the microsphere formulations of the present invention.

According to another aspect of the invention, there is provided a microsphere composition, comprising a cationic lipid of the invention, wherein the cationic lipid is incorporated as the transfection agent which is associated with the bioactive therapeutic factor composition. The lipids of the microsphere composition can further comprise a neutral lipid species selected from the group consisting of phosphatidylcholine, phosphatidylethanolamine, sphingomyelin, or cholesterol. A preferred molar ratio of cationic to neutral lipid species in these microsphere formulations is from about 9/1 to 1/9; a molar ratio of about 5/5 is particularly preferred. The microsphere formulation can further comprise a lyso lipid selected from the group consisting of lysophosphatidylcholine, lysophosphatidylethanolamine, or a lyso form of a cationic lipid species.

According to yet another aspect of the invention, there are provided pharmaceutical products comprising the microspheres conjugated to a bioactive therapeutic factor by means of any one of the cationic or amphiphilic lipids disclosed herein together with a pharmacologically effective amount of an additional therapeutic agent, such as a therapeutic drug. The cationic or amphiphilic lipids present in these compositions facilitate the intracellular delivery of the both the bioactive therapeutic factors and/or the additional active therapeutic agent. Products are provided for topical, enteral and parenteral uses. In one pharmaceutical product the additional therapeutic agent is for example, without limitation, a steroid; in another, the therapeutic agent is, for example, without limitation, a non-steroidal anti-inflammatory agent.

In other pharmaceutical products of the invention, the additional therapeutic agent is an antiviral nucleoside analogue or preferably a lipid derivative of an antiviral nucleoside analogue, which is a phosphatidyl derivative, or a diphosphate diglyceride derivative. The antiviral nucleoside can be a dideoxynucleoside, a didehydronucleoside, a halogenated or azido-derivative of a nucleoside, or an acyclic nucleoside. In preferred embodiments, the lipid derivatives of antiviral nucleosides are (3'-azido-3'-deoxy)thymidine-5'-diphospho-3-diacylglycerol (AZT diphosphate diglyceride) and dideoxythymidine diphosphate diglyceride. In particularly preferred embodiments, the lipid derivative of an antiviral nucleoside is an acyclovir or gancyclovir diphosphate diglyceride or diphosphate diglyceride derivatives of 1-(2-deoxy-2'-fluoro-1-.beta.-D-arabinofuranosyl)-5-iodocytosine (FIAC) or 1(2'-deoxy-2'-fluoro-1-.beta.-D-arabinofuranosyl)5-iodouracil (FIAU).

4.13 Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration. The reagents of any of the assays or methods described herein may also be included as components of a kit.

In one kit format, commercially available beads or microparticle of the present invention are present in a liquid physiologically compatible solution with a transfection agent and a polynucleotide encoding a bioactive therapeutic factor of the present invention, wherein all three components are present in one vial. In another kit format, a commercially available microparticle of the present invention may be available in one vial. The polynucleotide encoding the bioactive therapeutic factor associated with a transfection agent of the present invention may be present in another vial, wherein the microparticle is then mixed together with the polynucleotide transfection agent complex. Finally, in another kit format, commercially available beads or microspheres of the present invention are present in a liquid physiologically compatible solution in one vial. The commercially available transfection agent may be present in another separate vial. The polynucleotide encoding a bioactive therapeutic factor of the present invention may be present in yet another vial. The three components from the separate vials may then be combined to form the microparticle polynucleotide encoding a bioactive therapeutic factor associated with a transfection agent of the invention.

In yet another kit format, beads or microparticles of the present invention are present in a liquid physiologically compatible solution with polynucleotide encoding a bioactive therapeutic factor associated with a transfection agent which is in combination with a transfection enhancing agent. In yet another kit format, beads or microparticles of the present invention are present in a liquid physiologically compatible solution with polynucleotide encoding a bioactive therapeutic factor associated with a transfection agent which is in combination with an enhancer for absorption of the bioactive therapeutic agent.

The following examples are offered by way of illustration, and not by way of limitation.

5. EXAMPLES

Example 1

In a beaker containing 100 ml of demineralized water, 58 g of sodium chloride and 27 g of sodium acetate are dissolved. One adds 400 ml of glycerol and then the pH is adjusted between 5.9 and 6.1. Then 90 g of N-tris-hydroxy-methyl methylacrylamide, 35 mg of diethylaminoethylacryl-amide and 10 g of N,N-methylene-bis-acrylamide are added. One heats at 60-70 C and 100 mo of a hot 300 mg/ml gelatin solution is added. The total volume of the mixture is adjusted to 980 ml by addition of hot water and then 20 ml of a 70 mg/ml ammonium persulfate solution and 4 ml of N,N,N',N'-tetramethylethylenediamine are added.

This solution is poured into paraffin oil at 50-70 C stirring. After a few minutes, the polymerization reaction of acrylic monomers is manifested by an increase of temperature. The microspheres are then recovered by decanting, washed carefully, screened and sterilized in an autoclave in a buffered medium.

Those microspheres, after screen calibration, possess the characteristics desired for embolization, including a marked cationic charge and an effective adhesion agent (gelatin or denatured collagen).

Example 2

The procedure of Example 1 is followed, using triethylaminoethyl acrylamide instead of diethylaminoethyl acrylamide. After recovery of the spheres, the gelatin is reticulated by means of a 25% glutaraldehyde solution (100 ml of all of the microspheres). The treatment is carried out stirring at 4 C overnight. It is followed by a washing with demineralized water.

Examples 3 and 4

The procedure of Examples 1 and 2 is followed, replacing 10 g of N-tris-hydroxymethyl methylacrylamide with 10 g of acrylic acid. The microspheres obtained possess high swellability that is controllable by salt and ionic concentration and pH level. Those microspheres are advantageously usable in direct view of the user at the time of handling.

Examples 5 and 6

The procedure of Examples 1 and 2 is followed, replacing N-tris-hydroxymethyl methylacrylamide with 10 g of N-acryloyl hexamethylene Procion Red HE-3B. The microspheres obtained possess an intense red coloration due to the integration of the acrylic dye in the polymer lattice. Those microspheres are advantageously usable in direct view of the user at the time of handling.

Examples 7 and 8

One hundred milliliters of microspheres obtained according to Examples 1 to 4 are washed with a 0.1 M borate buffer of pH 8 and then suspended in 50 ml of a 5 mg/ml rhodamine isothiocyanate solution. The suspension is then stirred for at least 15 hours, after which it is washed with a neutral buffer to a colorless supernatant.

Those fluorescent red-colored microspheres are then calibrated and sterilized, and can be used in embolization gene therapy.

Examples 9 and 10

The procedure of Examples 1 to 4 is followed, replacing 10 g of N-tris-hydroxymethyl methylacrylamide with 10 g of a monomer opaque to X-rays, (acrylamido-3-propionamido)-3-triiodo-2,4,6-benzoic acid.

The microspheres obtained possess the property of absorbing X-rays and are therefore of particular interest in their in vivo follow-up after use in embolization gene therapy.

Examples 11 to 14

The procedure of Examples 1 to 2 is followed, adding to the initial monomer solution 5 g of a radio-opaque soluble linear polymer, acrylamino-3-triiodo-2,4,6-benzoic polyacid (Examples 11 and 12) or (acrylamino-3-propionamido)-3-triiodo-2,4,6-benzoic polyacid (Examples 13 and 14).

Those polymers, having a molecular weight exceeding 100,000 Dalton, are imprisoned in the polymer lattice and, without disturbing the general properties of the microspheres for the applications claimed, make it possible to attain a radiopacity usable for the in vivo follow-up of embolization gene therapy.

Examples 15 and 16

The procedure of Examples 1 and 2 is followed, adding to the initial monomer solution 200 g of barium sulfate power. The microspheres obtained are opaque to both visible light and X-rays.

Examples 17 and 18

The procedure of Examples 1 and 2 is followed, adding 50 mg of magnetite ($Fe_3O_4$) to the initial monomer solution.

The microspheres obtained have the property of being detected in Magnetic Resonance Imaging (MRI) imagery.

Example 21

Preparation of Injectable Suspension for Use in Embolization Gene Therapy

A further embodiment of the invention comprises using any of the microspheres of from examples 1-20 described supra and further mixing the microsphere with a polynucleotide coding for the p53 gene, under the control of a suitable promoter, where the polynucleotide is associated with a transfection agent such as Transfectam® (Biosphere Medical). Such microsphere/P53 gene/Transfectam® compositions are useful in the arteriolar embolization and amelioration, and subsequent elimination of various cancers such as, for example, liver, kidney and pancreatic cancer.

Example 22

Preparation of Injectable Suspension for Use in Combination Embolization Gene Therapy and Anti-Angiogenisis Therapy A further embodiment of the invention comprises using any of the microspheres of from examples 1-20 described supra and further mixing the microsphere with an anti-angiogenis agent encoded by a polynucleotide (under the control of a suitable promoter), where the polynucleotide is associated with a transfection agent such as Transfectam® (Biosphere Medical). Such microsphere/anti-angiogenisis agent/Transfectam® compositions are useful in the combined arteriolar embolization of a cancer and subsequent prevention of angiogenisis for the amelioration, and subsequent elimination of various cancers such as, for example, prostatic cancer.

The embodiments of the present invention described above are intended to be merely exemplary and those skilled in the art will recognize, or be able to ascertain using no more than routine experimentation, numerous equivalents to the specific procedures described herein. All such equivalents are considered to be within the scope of the present invention and are covered by the following claims.

The contents of all references described herein are hereby incorporated by reference. Other embodiments are within the following claims.

What is claimed is:

1. An MRI-detectable, substantially spherical microsphere suitable for active embolization, comprising:

an iron oxide particle;
a biocompatible, hydrophilic, non-biodegradable polymeric material, wherein the polymeric material comprises an acrylamide moiety and an ionic moiety; and
an anti-neoplastic agent, wherein the anti-neoplastic agent is associated with the polymeric material by an ionic interaction with the ionic moiety.

2. The microsphere of claim 1, wherein the anti-neoplastic agent is selected from at least one of doxorubicin, epirubicin or irinotecan.

3. The microsphere of claim 1, wherein the microsphere is cross-linked.

4. The microsphere of claim 3, wherein the cross-linking agent is N,N-methylene-bis-acrylamide.

5. The microsphere of claim 1, wherein the polymeric material comprises a copolymer comprising:
an acrylate polymer or a polyvinyl polymer, and
an acrylamide polymer.

6. The microsphere of claim 5, wherein the acrylamide polymer comprises N-tris-hydroxymethyl methylacrylamide.

7. The microsphere of claim 1, wherein the iron oxide particle is selected from at least one of: iron(II) oxide, iron (III) oxide, or mixtures thereof.

8. The microsphere of claim 1, wherein the iron oxide particle is a nanoparticle.

9. The microsphere of claim 1 wherein the microspheres are swellable and wherein the diameter of the microsphere ranges from about 10 μm to about 1000 μm before swelling.

10. The microsphere of claim 9, wherein the diameter of the microsphere ranges from about 30 μm to about 2000 μm after swelling.

11. An injectable composition comprising the microsphere of claim 1 and a biocompatible carrier, wherein the composition is sterile.

12. The composition of claim 11 where the composition is injectable through a needle of about 18 gauge or smaller.

13. A method for active embolization, comprising administering to a patient an MRI-detectable, substantially spherical microsphere comprising:
an iron oxide particle;
a biocompatible, hydrophilic, non-biodegradable polymeric material, wherein the polymeric material comprises an acrylamide moiety and an ionic moiety; and
a positively-charged drug, wherein the positively-charged drug is associated with the polymeric material by an ionic interaction with the ionic moiety.

14. The method of claim 13, wherein the drug is an anti-neoplastic agent.

15. The method of claim 14, wherein the drug is doxorubicin.

16. The method of claim 13, wherein administering to a patient comprises injecting a composition comprising the microsphere and a biocompatible carrier, wherein the composition is sterile.

17. The method of claim 16, wherein the composition is injectable through a needle of about 18 gauge or smaller.

18. The method of claim 13, wherein the microsphere is cross-linked.

19. The method of claim 18, wherein the cross-linking agent is N,N-methylene-bis-acrylamide.

20. The method of claim 13, wherein the polymeric material comprises a copolymer comprising:
an acrylate polymer or a polyvinyl polymer, and
an acrylamide polymer.

21. The method of claim 20, wherein the acrylamide polymer comprises N-tris-hydroxymethyl methylacrylamide.

22. The method of claim 13, wherein the iron oxide particle is selected from at least one of: iron(II) oxide, iron(III) oxide, or mixtures thereof.

23. The method of claim 13, wherein the iron oxide particle is a nanoparticle.

24. The method of claim 13 wherein the microspheres are swellable and wherein the diameter of the microsphere ranges from about 10 μm to about 1000 μm before swelling.

25. The method of claim 24, wherein the diameter of the microsphere ranges from about 30 μm to about 2000 μm after swelling.

* * * * *